(12) United States Patent
Nadobny et al.

(10) Patent No.: US 8,949,088 B2
(45) Date of Patent: Feb. 3, 2015

(54) COMPUTER-AIDED SIMULATION TOOL FOR PROVIDING ASSISTANCE IN THE PLANNING OF THERMOTHERAPY

(75) Inventors: Jacek Nadobny, Berlin (DE); Peng Liu, Berlin (DE); Jens-Thorsten Ollek, Berlin (DE); Heike C. Bender, Dorfen (DE)

(73) Assignee: Magforce AG, Berlin (DE)

(*) Notice: Subject to any disclaimer, the term of this patent is extended or adjusted under 35 U.S.C. 154(b) by 0 days.

(21) Appl. No.: 13/989,313

(22) PCT Filed: Mar. 8, 2012

(86) PCT No.: PCT/EP2012/001034
§ 371 (c)(1),
(2), (4) Date: Jan. 9, 2014

(87) PCT Pub. No.: WO2012/119775
PCT Pub. Date: Sep. 13, 2012

(65) Prior Publication Data
US 2014/0149092 A1    May 29, 2014

(30) Foreign Application Priority Data
Mar. 10, 2011  (EP) ..................................... 11001993

(51) Int. Cl.
*G06F 17/50*  (2006.01)
*G06F 19/00*  (2011.01)
(Continued)

(52) U.S. Cl.
CPC ........ *G06F 19/3437* (2013.01); *A61K 41/0052* (2013.01); *A61N 2/00* (2013.01); *A61N 1/406* (2013.01); *A61B 19/50* (2013.01); *A61K 9/5094* (2013.01)
USPC .................................................. 703/2; 703/6

(58) Field of Classification Search
USPC .......................... 703/2, 6; 424/497; 600/9, 10
See application file for complete search history.

(56) References Cited

U.S. PATENT DOCUMENTS 6,301,329 B1  10/2001  Surridge
6,385,477 B1   5/2002  Werner et al.
(Continued)

FOREIGN PATENT DOCUMENTS

EP          1 055 181 B1    5/2002
WO      WO 01/13949 A2    3/2001
(Continued)

OTHER PUBLICATIONS

International Search Report and Written Opinion received in PCT/EP2012/001034.
(Continued)

*Primary Examiner* — Kamini S Shah
*Assistant Examiner* — Luke Osborne
(74) *Attorney, Agent, or Firm* — The Marbury Law Group, PLLC

(57) ABSTRACT

The invention relates to a computer-aided simulation tool, in particular to computer-aided simulation methods, for providing assistance in the planning of thermotherapy, and to suitably configured computer equipment. The thermotherapy comprises hyperthermic treatment of a tumor volume within a volume of a human body. The hyperthermic treatment comprises the application of a magnetic field within a treatment volume by means of a magnetic field applicator. In at least one depot volume, thermal energy can be introduced by means of magnetic, paramagnetic and/or superparamagnetic nanoparticles deposited in the body, by power absorption in the applied magnetic field. Field strength values and optionally calculated temperature distributions are provided for assisting the user in the planning of the thermotherapy.

28 Claims, 9 Drawing Sheets

(51) Int. Cl.
  A61K 41/00 (2006.01)
  A61N 2/00 (2006.01)
  A61N 1/40 (2006.01)
  A61B 19/00 (2006.01)
  A61K 9/50 (2006.01)

(56) References Cited

U.S. PATENT DOCUMENTS

| | | | |
|---|---|---|---|
| 7,471,974 B2 | 12/2008 | Hartlep et al. | |
| 7,658,704 B2 | 2/2010 | Fox et al. | |
| 2003/0032995 A1* | 2/2003 | Handy et al. | 607/103 |
| 2008/0268061 A1 | 10/2008 | Jordan et al. | |
| 2011/0052609 A1 | 3/2011 | Waldoefner et al. | |

FOREIGN PATENT DOCUMENTS

| | | |
|---|---|---|
| WO | WO-2006/102307 A2 | 9/2006 |
| WO | WO-2007/113572 A1 | 10/2007 |
| WO | WO 2009/100716 A2 | 8/2009 |
| WO | WO 2011/082796 A2 | 7/2011 |

OTHER PUBLICATIONS

Falk, M. H. and R. D. Issels "Hyperthemia in oncology." (2001). *Int J Hyperthemia* 17(1): 1-18.

Frackowiak, R. S. J., et al. "Quantitative Measurement of Regional Cerebral Blood Flow and Oxygen Metabolism in Man Using 15O and Positron Emission Tomography: Theory, Procedure, and Normal Values." (1980). *Journal of Computer Assisted Tomography* 4(6): 727-736.

Gellermann, J., et al. "Clinical evaluation and verification of the hyperthermia treatment planning system hyperplan." (2000). *Int J Radiat Oncol Biol Phys.* 47(4): 1145-1156.

Gneveckow, U., et al. "Description and characterization of the novel hyperthermia- and thermoabalation-system MFH 300F for clinical magnetic fluid hyperthermia." (2004). *Med Phys.* 31(6): 1444-1451.

Hildebrant, B., et al. "The cellular and molecular basis of hyperthermia." (2002). *Critical Reviews in Ocology Hematology* 43(1): 33-56.

Hlavin, M. L. "Principles of Neurosurgery." (1994). *N Engl J Med* 331(23): 1597.

Johannsen, M., et al. "Thermotherapy of Prostate Cancer Using Magnetic Nanoparticles : Feasibility, Imaging, and Three-Dimensional Temperture Distribution",Eur Urol (2006), doi : 10.1016/j.eururo. Nov. 23, 2006.

Johannsen, M., et al., "Magnetic Nanoparticle Hyperthermia for Porstate Cancer", (2010) Int. J. Hyperthermia, (6 pages). Online research article, doi: 10.3109/02656731003745740.

Jordan, A., et al. "The effect of thermotherapy using magnetic nanoparticles on rat malignant glioma." (2005). J Neurooncol. 78(1): 7-14. Epub Nov. 29, 2005.

Jordan, A., et al. "Thermotherapie mit magnetischen Nanopartikeln." (2007). *Der Onkologe* 13(10): 894-902.

Kudo, K., et al. "Quantitative cerebral blood flow measurement with dynamic perfusion CT using the vascular-pixel elimination method: comparison with H2(15)O positron emission tomography." (2003). *AJNR Am J Neuroradiol* 24(3): 419-426.

Maier-Hauff, K., et al. "Intracranial thermotherapy using magnetic nanoparticles combined with external beam radiotherapy: results of a feasibility study on patients with glioblastoma multiforme." (2007). *J Neurooncol.* 81(1): 53-60. Epub Jun. 14, 2006.

Maier-Hauff, K., et al. "Efficacy and safety of intratumoral thermotherapy using magnetic iron-oxide nanoparticles combined with external beam radiotherapy on patients with recurrent glioblastoma multiforme" (2011). J Neurooncol 103(2): 317-324 Epub Sep. 16, 2010.

Nadobny, J. et al. "Evaluation of MR-Induced Hot Spots for Different Temporal SAR Modes Using a Time-Dependent Finite Difference Method With Explicit Temperature Gradient Treatment", (2007), IEEE Transactions on Biomedical Engineering, vol. 54, No. 10. pp. 1837-1850.

Thiesen, B. and A. Jordan "Clinical applications of magnetic nanoparticles for hyperthermia." (2008). *Int J Hyperthermia.* 24(6): 467-474.

Warmuth, C., et al. "Quantification of blood flow in brain tumors: comparison of arterial spin labeling and dynamic susceptibility-weighted contrast-enhanced MR imaging." (2003). *Radiology* 228(2): 523-532.

Wust, P., et al. "Hyperthermia in combined treatment of cancer." (2002). *Lancet Oncol* 3(8): 487-497.

Wust, P. et al., "Magnetic Nanoparticles for Interstitial Thermotherapy—Feasibility, Tolerance and Achieved Temperatures", (2006) *Int. J. Hyperthermia* , 22(8), pp. 673-685.

Sreenivasa, G., et al. "Clinical use of the hyperthermia treatment planning system HyperPlan to predict effectiveness and toxicity." (2003). *Int J Radiat Oncol Biol Phys.* 55(2): 407-419.

* cited by examiner

COMPUTER-AIDED SIMULATION TOOL FOR PROVIDING ASSISTANCE IN THE PLANNING OF THERMOTHERAPY

CROSS REFERENCE TO RELATED APPLICATIONS

The present application is a National Stage of International Application No. PCT/EP2012/001034 filed on Mar. 8, 2012, which claims the benefit of European Patent Application No. 11001993.2 filed on Mar. 10, 2011, the entire disclosures of which are incorporated herein by reference.

The invention relates to a computer-aided simulation tool for providing assistance in the planning of thermotherapy, and to be more precise to a computer-aided simulation method for providing assistance in thermotherapy planning and to computer devices of appropriate design.

PRIOR ART

Gneveckow et al., "Description and characterization of the novel hyperthermia- and thermoablation-system MFH® 300F for clinical magnetic fluid hyperthermia", Med. Phys. 31(6), June 2004, 1444 ff., describe, inter alia, the metrological determination of characteristic curves which indicate the relationship between the values of the magnetic field strength ("H field strength values" in kiloamps per meter, kA/m) and of the power absorption rates based on iron mass $SAR_{fe}$ ("Specific Absorption Rate of Iron", in watts per gram, W/g) for particular magnetic fluids. Further aspects of hyperthermia treatment on the basis of magnetic fluids are described (abstract; pages 1445-1446, section "II. Methods"; page 1447, section "IIIB. Power Absorption" in conjunction with FIG. 5; page 1448, section "IIID. Thermal distribution in the quasi-steady state"; pages 1449-1450, section "IV. Discussion").

Wust et al., "Magnetic nanoparticles for interstitial thermotherapy—feasibility, tolerance and achieved temperatures", Int. J. Hyperthermia, December 2006, 22(8), 673-685, describe a concept for hyperthermia treatment on the basis of magnetic fluids. The magnetic fluid contains iron oxide nanoparticles, dispersed in water. The magnetic fluid needs to be distributed in the tumor and is subsequently heated by the application of a magnetic alternating field by means of an applicator. Resultant temperature distributions are analyzed. Resultant values for the specific absorption rate in tissue (SAR) are ascertained from the particle distribution determined by means of computed tomography (CT) in combination with specific H field strength values in kA/m. The temperature distribution in the tumor area is calculated numerically by using a bioheat transfer equation (subsequently BHTE). The calculated temperature distribution is matched to directly measured temperature values at reference points in or close to the target area by means of a suitably chosen, average perfusion rate. (Abstract; page 675, section "Magnetic fluid"; page 677, section "Post-implantation analysis (PIA) and Thermotherapy").

Maier-Hauff et al., "Efficacy and safety of intratumoral thermotherapy using magnetic iron-oxide nanoparticles combined with external beam radiotherapy on patients with recurrent glioblastoma multiforme", J. Neurooncol. DOI 10/2007/s11060-010-0389-0, published online on Sep. 16, 2010, describe intratumoral thermotherapy methods using magnetic nanoparticles. A density of the nanoparticles after introduction is ascertained by means of CT methods. On the basis of the density distribution of the nanoparticles, the SAR thereof and an estimated perfusion rate within the tumor area, the generation of heat within the target tissue is determined as a function of a magnetic field strength by using a BHTE. The magnetic field strength (subsequently also called "H field strength" or just "field strength") should be chosen such that a temperature of 43° C. is not exceeded outside a border of 2 cm around the tumor. During treatments, direct temperature measurements were taken in a thermometry catheter positioned in advance. This monitors the observance of the limit temperature (abstract; page 3, FIG. 1 and left-hand column and right-hand column, $1^{st}$ paragraph).

Nadobny et al., "Evaluation of MR-Induced Hot Spots for Different Temporal SAR Modes Using a Time-Dependent Finite Difference Method With Explicit Temperature Gradient Treatment", IEEE Transactions on Biomedical Engineering, Vol. 54, No. 10, October 2007, pages 1837 ff., describes the numerical solution to a nonlinear BHTE in the time domain, which contains a temperature-dependent perfusion, and this is taken as the basis for performing numerical simulations for the temperature distribution in the human body (abstract; page 1837, section "I. Introduction"; page 1838, section "II. Time-Dependent BHTE"; pages 1840-1841, section IIIC: Thermal Simulation Procedures"; pages 1845-1846, sections "V. Discussion", "VI. Conclusion"). Inter alia, Nadobny et al. described a method (called a "decomposition way") according to which the BHTE is numerically solved by using the finite differences (FD) method to split the temperature distribution into a basal and an SAR-dependent part (page 1841, left-hand column, equations 5a, 5b and 6).

GENERAL ILLUSTRATION OF THE INVENTION

It is an object of the present invention to propose a tool for preparing thermotherapy which provides a doctor or other medical personnel with a comprehensive overview of different therapy options in order to facilitate a decision in favor of a particular option.

This object is achieved by an inventive computer-aided simulation tool for providing assistance in the planning of thermotherapy, and to be more precise by an inventive computer-aided simulation method for providing assistance in thermotherapy planning and also by computer devices of appropriate design.

The invention proposes a computer-aided simulation method for providing assistance in thermotherapy planning. The thermotherapy comprises (local/regional) hyperthermia treatment of a tumor volume in the body volume of a human body. The hyperthermia treatment comprises the application of a magnetic field in the treatment volume by means of a magnetic field applicator. In this case, thermal energy can be introduced into at least one "deposit volume", i.e. into a volume which contains nanoparticles, by power absorption in the applied magnetic field—by means of magnetic, paramagnetic and/or superparamagnetic nano-particles deposited in the body beforehand.

Accordingly, hyperthermia treatment within the context of the present invention is used generally to denote therapy by means of raised temperature. In the case of relatively small temperature rises up to approximately 45° C., this results in an increase in the effectiveness of chemotherapy and/or radiotherapy, hyperthermia in the narrower sense (Hildebrandt, B., et al. (2002). "The cellular and molecular basis of hyperthermia." Critical Reviews in Oncology Hematology 43(1): 33-56). In the case of temperature rises to more than 45° C., (tumor) cells die off directly, called thermoablation (Jordan, A., et al. (2006). "The effect of thermotherapy using magnetic nanoparticles on rat malignant glioma." J. Neurooncol. 78(1): 7-14. Epub 2005 Nov. 29).

It is desirable for the deposit volume or the deposit volumes to be situated fully or at least in part within the treatment volume, preferably the tumor volume. This should have been ensured by the preceding instillation of the nanoparticles. The tumor volume or the tumor volumes should be situated fully or in part in the treatment volume, according to the aim of therapy. Hence, the treatment volume is the volume which is meant to be heated by the hyperthermia primarily. Whether and to what extent this aim can probably be achieved is predicted by the inventive simulation method.

The inventive method is considered to be a simulation method for providing assistance in the planning and—optionally—control of thermotherapy, because it simulates the temperature distributions in the body which arise during treatment with the magnetic field applicator without such treatment actually being performed. The method thus requires no calibration, for example, by measured values which are measured for a treatment that is currently taking place. The results which are delivered by the inventive simulation tool can be used to draw conclusions about treatment parameters for a subsequent actual treatment, e.g. in relation to the field strength value or H field strength value that needs to be chosen.

The user of the inventive method or simulation tool may be a doctor, e.g. a radiologist or a radiotherapist, personnel with technical and/or medical training who have been trained to use a magnetic field applicator, or other users.

The nanoparticles may generally be particles which interact in some way with a magnetic field such that (following instillation of the particles into the body) tissue is heated. By way of example, they may be magnetic, paramagnetic or superparamagnetic nanoparticles, e.g. iron oxide nanoparticles with or without a coating. The particles may have any spatial forms, and may be at least essentially spherical, spheroidal, ellipsoidal, prismoidal or parallelepipedal in shape, for example. Although the particles are called 'nanoparticles' here, this term is meant to cover not only particles having dimensions (e.g. smallest or largest radius or diameter) in the nanometer range but also particles having other dimensions, for example particles having dimensions in the micron range. Preference is given to iron oxide nanoparticles having a diameter (determined under an electron microscope) of up to 100 nm.

The inventive simulation method comprises the following steps: in a first calculation step, also called "T selection" ("T" stands for temperature), calculation of a field strength value or H field strength value that needs to be set on the applicator on the basis of a geometric distribution of the nanoparticles and at least one prescribed temperature limit value which is not meant to be exceeded by the hyperthermia treatment; in an optional second calculation step, also called "H controller" ("H" stands for magnetic field strength) or "fast H controller" depending on the embodiment, calculation of a (resultant) temperature distribution that is to be expected for at least some of the body volume for each H field strength value from a plurality of prescribed H field strength values, and/or a user-defined H field strength value, preferably, in an optional third calculation step ("H selection"), automatic calculation of a temperature distribution that is to be expected for a maximum admissible H field strength value when the H field strength value calculated in the first calculation step is greater than this maximum admissible H field strength value; and provision (for the user) of the calculated H field strength value that needs to be set on the applicator and optionally of at least one calculated resultant temperature distribution, e.g. that associated with the aforementioned H field strength value, in order to provide assistance for the user in planning the thermotherapy.

In particular variants of the inventive simulation method, the prescribed temperature limit value or one of a plurality of prescribed temperature limit values relates to a maximum temperature or a temperature maximum only within the treatment volume that is to be heated. By way of example, the prescribed temperature limit value may relate to a temperature maximum in a range from 60° C. to 100° C., preferably 70° C. to 90° C., particularly 80° C., in the treatment volume.

In addition or as an alternative, the prescribed temperature limit value or one of a plurality of prescribed temperature limit values may relate to a temperature maximum outside the treatment volume that is to be heated. By way of example, the prescribed temperature limit value may relate to a temperature maximum in a range from 40° C. to 45° C., particularly 43° C., outside the treatment volume.

In some embodiments of the inventive simulation method, two prescribed temperature limit values which each relate to different volumes are used in the first calculation step. By way of example, one prescribed temperature limit value within the treatment volume may relate to a temperature maximum of 80° C. and another prescribed temperature limit value outside the treatment volume may relate to a temperature maximum of 43° C. In this case, the two prescribed temperature limit values can preferably be used simultaneously in the first calculation step.

A third calculation step ("H selection") may involve a temperature distribution that is to be expected being calculated for an H field strength value that is defined as maximum admissible. The H field strength value defined as maximum admissible may relate to an H field strength value that can be set as a maximum on the applicator, for example, or to an H field strength value for a patient that is defined as maximum admissible. The third calculation step can, on the basis of the calculation result of the first calculation step (T selection), be performed automatically when the H field strength value calculated in the first calculation step is greater than the H field strength value defined as maximum admissible.

In particular variants of the inventive simulation method, no temperature limit value is used in the calculations in the second calculation step (H controller; fast H controller) and/or in the third calculation step (H selection). During these calculations, the possibly resultant simulated temperature distributions may therefore exceed the limit value(s) considered in the first calculation step. For example, temperatures higher than 43° C. may thus occur outside the treatment volume and/or temperatures higher than 80° C. may thus occur inside the treatment volume. This allows the doctor to have a more comprehensive overview of the effects of the planned thermal therapy than if he had only strictly temperature-limit-value-based results for the calculation from the first calculation step.

The calculations in the second calculation step can be performed for a plurality of prescribed H field strength values that can be set on the applicator, preferably between 3 and 20 H field strength values, particularly between 5 and 10 H field strength values. In addition or as an alternative, the calculations in the second calculation step can be performed for a plurality of prescribed H field strength values that can be set on the applicator, preferably between 3 kA/m and 20 kA/m, particularly preferably between 5 kA/m and 10 kA/m (H controller).

The second calculation step (H controller; fast H controller) can be initiated after the first calculation step (T selection) and possibly the third calculation step (H selection) only by a user input. If the user requires no further orientation after the output of the initial resultant temperature distribution with the associated initial H field strength value (in this case, "initially" means the result of the first or possibly the third calculation step), the user can dispense with a user input and in this way it is possible to save or otherwise use resources of the computer device on which the inventive simulation method is implemented.

Particularly in the case of the calculation of the H field strength value that is to be set in the first calculation step (T selection), variants of the inventive simulation method do not perform numerous iterations on the basis of the "trial and error" principle which involve resultant temperature distributions from chosen field strength values being calculated by means of a numerical solution to the BHTE so as to iteratively arrive at the sought H field strength value. Such iterations in which a BHTE is numerically solved each time require very many resources in terms of computation power, computation time and memory requirement and are therefore not suitable for a simulation tool which is intended to provide a user with an overview of planned therapy options. Instead, the BHTE is numerically solved just exactly twice in the first calculation step, as explained further below.

In one embodiment of the inventive simulation method, the H field strength value is calculated in the first calculation step (T selection) on the basis of a prescribed characteristic curve—for example derived from a reference measurement—which indicates a relationship between (reference) power absorption rate and H field strength.

In one specific variant of this embodiment, the first calculation step has the following steps: calculation of an average power absorption density (or of an equivalent variable) in the applicator magnetic field in the deposit volume, wherein the relative power absorption density (or an equivalent variable) is calculated on the basis of a measured geometric distribution of the nanoparticles, a BHTE describing the model is numerically solved precisely once in order to obtain a basal temperature distribution without power absorption, and a BHTE describing the model is numerically solved precisely once in order to obtain a relative temperature increment distribution on the basis of the relative power absorption density; and wherein the relative power absorption density is scaled by a temperature-based scaling factor which is obtained on the basis of the at least one prescribed temperature limit value, the basal temperature distribution and the relative temperature increment distribution; calculation, on the basis of the calculated average power absorption density and the calculated mass of the nanoparticles, of a reference power absorption rate which indicates the specific power absorption rate of an undiluted magnetic fluid containing the nanoparticles, for example, usually based on the mass of the nanoparticles in W/g; and calculation of an H field strength value on the basis of the calculated reference power absorption rate and a prescribed characteristic curve—for example derived from a reference measurement—which relates to a relationship between reference power absorption rate and applied H field strength; furthermore, as an option, calculation of the resultant temperature distribution on the basis of the basal temperature distribution, the relative temperature increment distribution and the temperature-based scaling factor.

The basal temperature distribution calculated in the first calculation step and/or the relative temperature increment distribution can be provided for at least one further use beyond the first calculation step, for example can be stored in the main memory and/or on a hard disk. By way of example, the use may relate to the fast calculation, in the second calculation step (for the "fast H controller" embodiment), of a resultant temperature distribution on the basis of an H field strength value that has been input by the user, without the BHTE needing to be numerically solved again in order to obtain the temperature distribution and/or the relative temperature increment distribution.

In the second calculation step in the "fast H controller" embodiment, regardless of the number of prescribed and/or user-defined H field strength values, a provided (previously calculated in the first calculation step) basal temperature distribution and/or provided (previously calculated in the first calculation step) relative temperature increment distribution can be used, for example the aforementioned temperature distributions (basal and relative incremental) which are provided from the first calculation step. Hence, it is possible to prevent the BHTE from being numerically solved again—which is intensive in terms of memory and computation time—for the calculation of the basal and/or relative incremental temperature distribution.

In particular embodiments of the inventive simulation method ("H controller" embodiment), the second calculation step is designed such that the basal temperature distribution and the relative incremental temperature distribution are not used from the main memory or from the hard disk but rather need to be recalculated as part of the second calculation step by numerically solving the BHTE. In this case, regardless of the number of prescribed and/or user-defined H field strength values, the BHTE is numerically solved no more than twice, namely once to calculate the basal temperature distribution and once to calculate the relative temperature increment distribution.

In variants of the inventive simulation method, in the second calculation step (H controller, fast H controller) the resultant temperature distribution that is to be expected is calculated by means of power-absorption-based scaling ("K") of a calculated or provided relative temperature increment distribution. Specific embodiments of the simulation method comprise the following steps in the second calculation step (H controller, fast H controller): calculation of a relative power absorption density distribution (or of an equivalent variable) and a relative average power absorption density (or an equivalent variable) on the basis of a measured geometric distribution of the nanoparticles; provision of a basal temperature distribution on the basis of a numerical solution to a BHTE describing the model without power absorption, and provision of a relative temperature increment distribution on the basis of a numerical solution to a BHTE describing the model with the calculated relative power absorption density distribution [the provision is made by reading in the previously stored distributions (for the "fast H controller") or by numerically solving the BHTE again (for the "H controller")]; performance of the following steps for each H field strength value from the plurality of prescribed H field strength values and/or the user-defined H field strength value: calculation of a reference power absorption rate which indicates the specific power absorption rate of an undiluted magnetic fluid containing the nanoparticles, for example, wherein the calculation is based on the respective H field strength value and a prescribed characteristic curve—for example derived from a reference measurement—which relates to a relationship between reference power absorption rate and applied H field strength; calculation, on the basis of the reference power absorption rate and the calculated mass of the nanoparticles in the deposit volume, of an average power absorption density; power-absorption-based scaling, i.e. calculation of a power-absorption-based scaling factor on the basis of the respective average power absorption density and the relative power absorption density; calculation of a respective resultant temperature distribution on the basis of the basal temperature distribution, the relative temperature increment distribution and the power-absorption-based scaling factor.

According to the invention, a further computer-aided simulation method (T selection) for providing assistance in thermotherapy planning is proposed. The thermotherapy comprises hyperthermia treatment of a tumor volume in a body volume of a human body. The hyperthermia treatment comprises the application of a magnetic field in a treatment volume by means of a magnetic field applicator. Thermal energy can be introduced into at least one deposit volume by power absorption in the applied magnetic field by means of magnetic, paramagnetic and/or superparamagnetic nanoparticles deposited in the body. The simulation method relates to the calculation of an H field strength that needs to be set on the applicator on the basis of a geometric distribution of the nanoparticles and at least one prescribed temperature limit value which is not meant to be exceeded by the hyperthermia treatment (T selection). The H field strength value is calculated on the basis of a prescribed characteristic curve—for example derived from a reference measurement—which indicates the relationship between power absorption rate and H field strength.

In one particular embodiment, the simulation method has the following steps: calculation of an average power absorption density (or of an equivalent variable) in the applicator magnetic field in the deposit volume, wherein a relative power absorption density is calculated on the basis of a measured geometric distribution of the nanoparticles, a BHTE describing the model is numerically solved precisely once in order to obtain a basal temperature distribution without power absorption, and a BHTE describing the model which is numerically solved precisely once in order to obtain a relative temperature increment distribution on the basis of the relative power absorption density; and wherein the relative power absorption density is scaled by a temperature-based scaling factor which is obtained on the basis of the at least one prescribed temperature limit value, the basal temperature distribution and the relative temperature increment distribution; calculation, on the basis of the calculated average power absorption density and the calculated mass of the nanoparticles, of a reference power absorption rate which indicates the specific power absorption rate of an undiluted magnetic fluid containing the nano-particles, for example; calculation of an H field strength value on the basis of the calculated reference power absorption rate and a prescribed characteristic curve—for example derived from a reference measurement—which relates to a relationship between reference power absorption rate and applied H field strength; preferably, calculation of the resultant temperature distribution on the basis of the basal temperature distribution, the relative temperature increment distribution and the temperature-based scaling factor; and provision of the calculated H field strength value and optionally the resultant temperature distribution associated with said H field strength value, calculated as described above, in order to provide assistance for the user in planning the thermotherapy.

The invention proposes yet a further computer-aided simulation method (H controller; fast H controller) for providing assistance in thermotherapy planning. The thermotherapy comprises hyperthermia treatment of a tumor volume in the body volume of a human body. The hyperthermia treatment comprises the application of a magnetic field in a treatment volume by means of a magnetic field applicator. Thermal energy can be introduced into at least one deposit volume by power absorption in the applied magnetic field by means of magnetic, paramagnetic and/or superparamagnetic nanoparticles deposited in the body. The simulation method relates to the calculation, for each H field strength value from a plurality of prescribed H field strength values and/or a user-defined H field strength value, of a temperature distribution that is to be expected for at least some of the body volume (H controller). The temperature distribution that is to be expected is calculated by means of power-absorption-based scaling of a calculated or provided relative temperature increment distribution.

In particular variants, regardless of the number of prescribed and/or user-defined H field strength values, e.g. in order to avoid numerically solving the BHTE again, a previously calculated (in the T selection step) basal temperature distribution and/or a previously calculated (in the T selection step) relative temperature increment distribution is/are used (fast H controller). In addition or as an alternative, it is possible—regardless of the number of prescribed and/or user-defined H field strength values—for a BHTE describing the model to be numerically solved never (fast H controller), once (H selection) or no more than twice (H controller) in order to subsequently determine the resultant temperature distribution. In the "never" case (fast H controller), the resultant temperature distribution is compiled from the basal temperature distribution—previously calculated (earlier calculation steps) by means of BHTE—and the previously calculated relative temperature increment distribution by means of power-absorption-based scaling. In the "once" case (H selection), the resultant temperature distribution is numerically calculated directly, i.e. without splitting into basal and incremental components, by solving the BHTE. In the "twice" case (H controller), the basal and incremental temperature distributions are numerically calculated in this (second) calculation step individually by solving the BHTE and are then compiled to produce the resultant temperature distribution by means of power-absorption-based scaling.

In particular embodiments, the simulation method has the following steps: calculation of a relative power absorption density distribution (or of an equivalent variable) and a relative average power absorption density (or an equivalent variable) on the basis of a measured geometric distribution of the nanoparticles; provision of a basal temperature distribution on the basis of a numerical solution to a BHTE describing the model without power absorption, and provision of a relative temperature increment distribution on the basis of a numerical solution to a BHTE describing the model with the calculated relative power absorption density distribution; performance of the following steps for each H field strength value from the plurality of prescribed H field strength values and/or the user-defined H field strength value: calculation of a reference power absorption rate which indicates the specific power absorption rate of an undiluted magnetic fluid containing the nanoparticles, for example, wherein the calculation is based on the respective H field strength value and a prescribed characteristic curve—for example derived from a reference measurement—which relates to a relationship between reference power absorption rate and applied H field strength; calculation, on the basis of the reference power absorption rate and the calculated mass of the nanoparticles in the deposit volume, of an average power absorption density; power-absorption-based scaling, i.e. calculation of a power-absorption-based scaling factor on the basis of the respective average power absorption density and the relative power absorption density; calculation of the respective resultant temperature distribution on the basis of the basal temperature distribution, the relative temperature increment distribution and the power-absorption-based scaling factor; provision of the calculated temperature distributions in order to provide assistance for the user in planning the thermotherapy.

The invention also proposes a computer program which prompts the execution of one of the simulation methods described herein when the computer program is executed on a programmable computer device, for example a computer in a clinic or doctor's practice. The computer program may be stored or present in stored form on a machine-readable data storage medium, for example a permanent or rewritable medium in or associated with a programmable computer device or a CD-ROM, DVD or a USB stick. In addition or as an alternative, the computer program can be provided for download onto a programmable computer device, for example via a data network such as the Internet or a communication link such as a telephone line and/or a wireless connection.

Furthermore, the invention provides a computer device which is designed to provide assistance in thermotherapy planning. In this case, the thermotherapy comprises hyperthermia treatment of a tumor volume in the body volume of a human body, wherein the hyperthermia treatment comprises the application of a magnetic field in the treatment volume by means of a magnetic field applicator. In this case, thermal energy can be introduced into at least one deposit volume by power absorption in the applied magnetic field by means of magnetic, paramagnetic and/or superparamagnetic nanoparticles deposited in the body. The computer device has the following components: a first calculation component which is designed to calculate an H field strength value that needs to be set on the applicator on the basis of a geometric distribution of the nanoparticles and at least one prescribed temperature limit value which is not meant to be exceeded by the hyperthermia treatment; a second calculation component which is designed to optionally calculate a temperature distribution that is to be expected for at least some of the body volume for each H field strength value from a plurality of prescribed H field strength values, and/or a user-defined H field strength value; an optional third component designed to calculate a temperature distribution that is to be expected for a maximum admissible H field strength value when the H field strength value calculated in the first calculation step is greater than this maximum admissible H field strength value; and a component for providing (the user with) the calculated H field strength value that needs to be set on the applicator and optionally at least one calculated temperature distribution (e.g. associated with the aforementioned H field strength value) in order to provide assistance for the user in planning the thermotherapy.

A further inventive computer device ("T selection") is designed to provide assistance in thermotherapy planning, wherein the thermotherapy comprises hyperthermia treatment of a tumor volume in a body volume of a human body and wherein the hyperthermia treatment comprises the application of a magnetic field in a treatment volume by means of a magnetic field applicator. In this case, thermal energy can be introduced into at least one deposit volume by power absorption in the applied magnetic field by means of magnetic, paramagnetic and/or superparamagnetic nanoparticles deposited in the body. The computer device has a component which is designed to calculate an H field strength that needs to be set on the applicator on the basis of a geometric distribution of the nanoparticles and at least one prescribed temperature limit value which is not meant to be exceeded by the hyperthermia treatment. In this case, the component has a module for calculating the H field strength value on the basis of a prescribed characteristic curve—for example derived from a reference measurement—wherein the characteristic curve indicates a relationship between power absorption rate and H field strength. In one preferred inventive variant of the computer device, the computer device has the following modules: a module for calculating an average power absorption density in the applicator magnetic field in the deposit volume, wherein a relative power absorption density is calculated on the basis of a measured geometric distribution of the nanoparticles, a BHTE describing the model is numerically solved precisely once in order to obtain a basal temperature distribution without power absorption, and a BHTE describing the model is numerically solved precisely once in order to obtain a relative temperature increment distribution on the basis of the relative power absorption density; and wherein the relative power absorption density is scaled by a temperature-based scaling factor which is obtained on the basis of the at least one prescribed temperature limit value, the basal temperature distribution and the relative temperature increment distribution; a module for calculating, on the basis of the calculated average power absorption density and the calculated mass of the nanoparticles, a reference power absorption rate which indicates the specific power absorption rate of an undiluted magnetic fluid containing the nanoparticles, for example; a module for calculating an H field strength value on the basis of the calculated reference power absorption rate and a prescribed characteristic curve—for example derived from a reference measurement—which relates to a relationship between reference power absorption rate and applied field strength; optionally, a module for calculating the resultant temperature distribution on the basis of the basal temperature distribution, the relative temperature increment distribution and the temperature-based scaling factor; a module for providing the calculated field strength value in order to provide assistance for the user in planning the thermotherapy; and optionally a module for providing the resultant temperature distribution associated with the calculated H field strength value in order to provide assistance for the user in planning the thermotherapy.

A further inventive computer device ("H controller", "fast H controller") is designed to provide assistance in thermotherapy planning, wherein the thermotherapy comprises hyperthermia treatment of a tumor volume in a body volume of a human body and wherein the hyperthermia treatment comprises the application of a magnetic field in a treatment volume by means of a magnetic field applicator. In this case, thermal energy can be introduced into at least one deposit volume by power absorption in the applied magnetic field by means of magnetic, paramagnetic and/or superparamagnetic nanoparticles deposited in the body. The computer device has a component which is designed to calculate, for each field strength value from a plurality of prescribed field strength values and/or a user-defined field strength value, a temperature distribution that is to be expected for at least some of the body volume. In this case, the component has a module for calculating the temperature distribution that is to be expected by means of power-absorption-based scaling of a calculated or provided temperature increment distribution. Preferably, the component is designed to calculate the temperature distribution that is to be expected in order to use, regardless of the number of prescribed and/or user-defined H field strength values, a provided (previously calculated in the T selection step) basal temperature distribution and/or a provided (previously calculated in the T selection step) relative temperature increment distribution (fast H controller).

With further preference, the component for calculating the temperature distribution that is to be expected is designed to calculate, regardless of the number of prescribed and/or user-defined field strength values, no more than two temperature distributions (H controller), namely a basal temperature distribution and/or a relative temperature increment distribution.

With further preference, the inventive computer device has the following modules ("H controller", "fast H controller"): a module for calculating a relative power absorption density distribution and a relative average power absorption density on the basis of a measured geometric distribution of the nanoparticles; a module for providing a basal temperature distribution on the basis of a numerical solution to a BHTE describing the model without power absorption, and providing a relative temperature increment distribution on the basis of a numerical solution to a BHTE describing the model with the calculated relative power absorption density distribution; a module for performing the following steps for each H field strength value from the plurality of prescribed H field strength values: calculation of a reference power absorption rate which indicates the specific power absorption rate of an undiluted magnetic fluid containing the nanoparticles, for example, wherein the calculation is based on the respective H field strength value and a prescribed characteristic curve—for example derived from a reference measurement—which relates to a relationship between reference power absorption rate and applied H field strength; calculation, on the basis of the reference power absorption rate and the calculated mass of the nanoparticles in the deposit volume, of an average power absorption density; power-absorption-dependent scaling, i.e. calculation of a power-absorption-based scaling factor on the basis of the respective average power absorption density and the relative power absorption density; calculation of a respective resultant temperature distribution on the basis of the basal temperature distribution, the relative temperature increment distribution and the power-absorption-based scaling factor; and a module for providing the calculated temperature distributions in order to provide assistance for the user in planning the thermotherapy.

Furthermore, the invention proposes a system which comprises a computer device as outlined above and a magnetic field applicator or the parts thereof. The inventive computer device may be designed for use with the magnetic field applicator, for example by virtue of the use of, by way of example, an H field strength that can be set on the applicator as a maximum and/or metrological input data, such as a characteristic curve derived from a reference measurement, for example, for the power absorption on the basis of the H field strength. The magnetic field applicator can be matched to the inventive computer device by virtue of the applicator accepting data from said applicator, such as an H field strength value that needs to be set (for example after the end of the simulations as a default value and/or by the instigation of the user). For this embodiment, the computer device can also be used for planning or control.

The invention also proposes a system which comprises a computer program as outlined above, a data storage medium as outlined above, a computer device as outlined above or a system as outlined above, and which also comprises a magnetic fluid which contains magnetic nanoparticles. The inventive computer program may match the use of the magnetic fluid by virtue of the power absorption v. H field strength for this specific characteristic curve being used for the simulations. The computer program may be designed for the use of a plurality of magnetic fluids; in this case, the user would need to input the fluid that is actually to be used before the start of the simulations, for example by selecting from a menu in a GUI of the computer device.

Instead of in a magnetic fluid, the nanoparticles could, in principle, also be instilled into the body of the patient in another form of presentation. All forms of presentation are intended to be covered by the invention.

A further subject of the invention comprises a method for controlled heating of an organ or tissue, having the following steps: introduction of magnetic, paramagnetic and/or superparamagnetic nanoparticles into an organ volume or tissue volume; ascertainment of the nanoparticle quantity and/or distribution in the organ volume or tissue volume; calculation of an H field strength that needs to be set on the basis of one of the appropriate methods outlined above or of a resultant temperature distribution on the basis of one of the appropriate methods outlined above; and deposition of thermal energy by means of application of a magnetic field, wherein the applied H field strength is set, which corresponds to the calculated field strength or to the field strength derived from a calculated temperature distribution, in each case with a deviation of +/−10%, preferably +/−5%, particularly +/−1%. This method can be performed in vitro if appropriate.

A method for treating a tumor in a patient contains the following steps: introduction of a suitable quantity of magnetic, paramagnetic and/or superparamagnetic nanoparticles into a tumor volume; ascertainment of the nanoparticle quantity and/or distribution in the tumor volume; calculation of a field strength that needs to be set on the basis of one of the appropriate methods outlined above or of a resultant temperature distribution on the basis of one of the appropriate methods outlined above; deposition of thermal energy by means of application of a magnetic field, wherein the applied field strength is set, which corresponds to the calculated field strength or the field strength derived from a calculated temperature distribution, in each case with a deviation of +/−10%, preferably +/−5%, particularly +/−1%.

Suitable methods for treating tumors or for controlled heating of an organ or tissue by means of suitable nanoparticles and application of a magnetic field that are able to be improved by the inventive simulation methods are known from the prior art. For example, Maier-Hauff et al. (2010, supra) describe a successful study on 66 patients with brain tumors, 59 of them with glioblastoma. Furthermore, similar methods were successfully performed on prostate carcinoma patients (Johannsen, M., et al. (2007), Eur Urol. 52(6): 1653-61. Epub 2006 Nov. 17; Johannsen, M., et al. (2010), Int J Hyperthermia 26(8): 790-5.) and also in a study in which patients with various tumors, namely chondrosarcoma, rectal carcinoma, cervical carcinoma, rhabdomyosarcoma, parapharyngeal sarcoma and prostate carcinoma, were included and treated (Wust, P., et al. (2006), Int J. Hyperthermia. 22(8): 673-85.). Clinical data from suitable methods are summarized in Thiesen, B. and A. Jordan (2008, Int J. Hyperthermia. 24(6): 467-74). Further methods for the treatment of tumors or for the controlled heating of an organ or tissue by means of suitable nanoparticles and application of a magnetic field are known from US 20080268061, US 20110052609, WO 2009/100716 and WO 2011/082796. Solid tumors are preferred, particularly local and locally advanced tumors, or systemic tumor diseases, which cause local problems such as inoperable metastases. Examples are brain tumors, e.g. glioblastoma and astrocytoma, brain metastases, prostate cancer, pancreatic cancer, hepatocellular carcinoma, throat and neck tumors, cancer of the bladder, stomach cancer, intestinal cancer, renal cell carcinoma, ovarian carcinoma, cervical carcinoma, sarcomas, basal cell carcinoma and melanoma.

The inventive methods for the controlled heating of an organ or tissue can be used for the treatment of arthrosis, arthritis and other rheumatic joint diseases, for example. The treatment of these diseases by means of similar methods is known from WO 01/13949, for example.

Advantages of the Invention

The invention provides the user with extensive opportunities for obtaining an overview of various therapy options and the effects thereof and planning the therapy accordingly. To this end, the inventive simulation tool automatically provides a temperature distribution which has been calculated on the basis of a maximum field strength, but taking account of prescribed/input temperature limit values. The invention allows two (or more) limit values to be taken into account, e.g. a maximum temperature outside the treatment area, in order to look after the healthy tissue, and/or maximum temperature inside the treatment area, in order to destroy the tumor but nevertheless to limit an input of power into the body of the patient. In principle, it is conceivable to prescribe a geometric temperature limit value distribution which takes account of special features specific to tissue, for example.

The inventive simulation tool may be "intelligent" in the sense that it rejects the resultant field strength value if it is greater than a maximum settable value on the applicator/for a given patient, for example. In this case, the simulation tool calculates a new temperature distribution afresh on the basis of the maximum settable field strength value.

The user can decide whether he wishes to use the field strength value resulting therefrom without performing further simulations. As a result, the inventive simulation tool provides the experienced user with the opportunity to terminate the planning without wasting resources. It is then already possible to use the simulation tool for the next patient, for example.

The user can also decide to obtain a more extensive overview. In this case, the simulation tool can calculate temperature distributions for a plurality of field strength values, for example. These calculations can be performed in the background as soon as the user has made an appropriate input (if applicable, the simulation tool can also be configured such that it automatically starts these calculations in the background after the initial temperature distribution has been provided). It is therefore already possible for the user to work with the results from the first calculation step without delay.

These temperature distributions do not take account of the temperature limit values discussed above. Hence, the user is in this case provided with an extensive decision basis by means of the effects of particular field strength settings and, depending on the aim of the therapy, the severity of the disease, the tissue that is possibly affected, etc., may under some circumstances decide upon a therapy option in which the temperature limit value or the limit values are not observed everywhere.

In addition or as an alternative, the simulation tool accepts a field strength value that is input by the user and calculates the resultant temperature distribution for said field strength value. In particular embodiments of the invention, this is accomplished in time-saving fashion without numerically solving the BHTE again, which means that the result is available to the user essentially without any waiting time, for example after just one second or less.

By means of the inventive simulation tool, the aim of therapy and possible side effects can thus be predicted better and more easily and can thus also be controlled better and more extensively.

In this case, the inventive simulation tool requires—both for calculating the temperature distribution using prescribed temperature limit values (first calculation step, see below temperature selection or "T selection") and for calculating a scale of temperature distributions or a user-defined field strength value (second calculation step, see below H field strength controller, "H controller" or "fast H controller")—precisely two numerical solutions to a BHTE with subsequent scaling, that is to say manages without iterative trial and error approximations (by means of recurrently restarted numerical solutions to the BHTE) to the sought field strength value in the first step and calculate the relevant temperature distributions by means of simple scaling for an arbitrary number of field strength values, in principle, in the second step. As a result, the simulation tool is user friendly because the calculation results are available extremely precisely and nevertheless quickly. The inventive simulation tool requires only a fraction of the CPU computation time in comparison with an iterative trial and error approach and therefore makes a clinically feasible application possible in the first place, even using computers which are older/have limited resources.

BRIEF DESCRIPTION OF THE FIGURES

Further aspects and advantages of the invention will now be described in more detail with reference to the appended figures, in which.

EXEMPLARY EMBODIMENTS OF THE INVENTION

Figure 1:
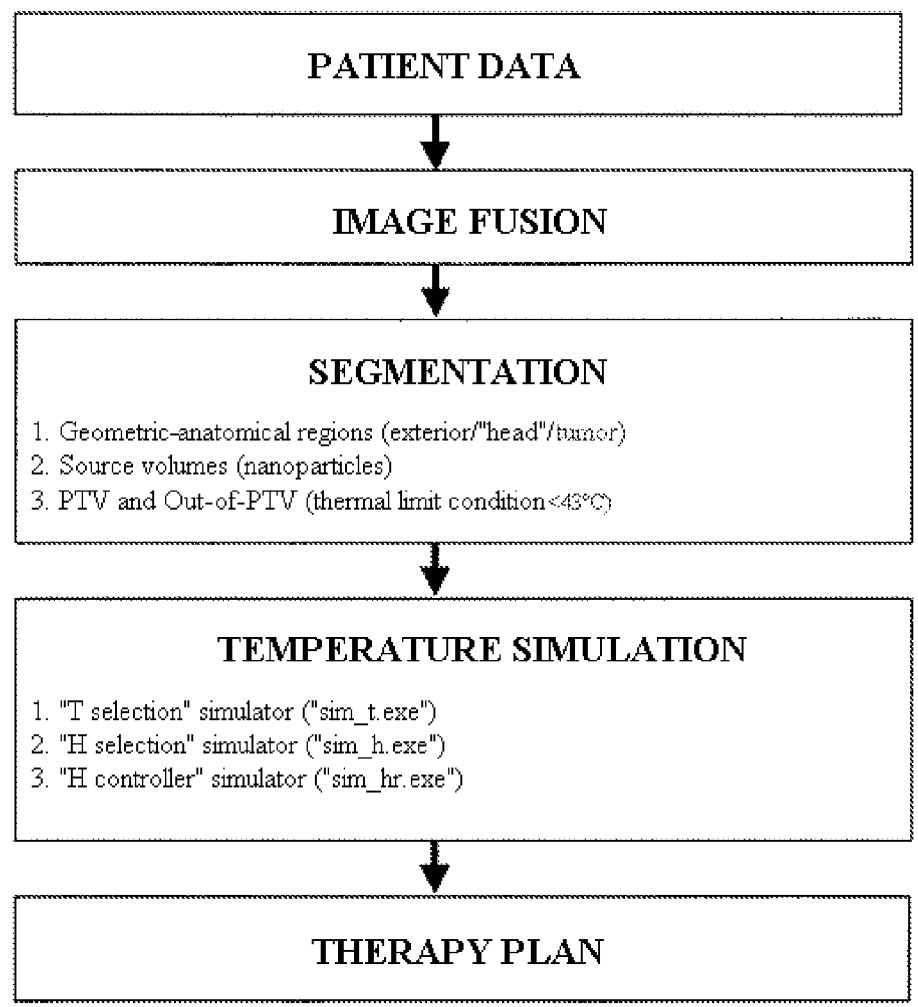
FIG. 1 shows a flowchart for a general program cycle from a first exemplary embodiment of an inventive simulation tool having the following main steps: "patient data", "image fusion", "segmentation", "temperature simulation" and "therapy plan". In the main step, "temperature simulation", the "temperature simulator" program package (called "simulator" for short) is called. In the first exemplary embodiment (FIG. 1 to FIG. 5), the simulator package contains three autarkic simulator (execution) programs (.exe), but the simulator can also be executed as a linkable program library having three main subroutines ("mainsubroutines") (see second exemplary embodiment FIG. 6 to FIG. 9)

The text below describes a first exemplary embodiment of an inventive simulation tool in more detail. FIG. 1 shows a schematic representation of a program cycle from an inventive simulation method in the form of a piece of simulation software which has been developed with the aim of providing assistance in NanoTherm® therapy.

The software provides the treating doctor (neurosurgeon, radiologist) with orientation assistance during thermotherapy for malignant tumors, such as brain tumors, in order to estimate the treatment temperatures and the magnetic field strength required therefor on the basis of a BHTE that describes the model.

In order to estimate the therapy field strength, the software provides the opportunity to import and register image data in DICOM format, e.g. from MRI and CT scans. It is likewise possible to perform contouring operations on all image files used (segmentation).

The software takes the user to the result in steps by querying the required parameters. This involves firstly 3D visualization, which reveals the contoured areas such as a tumor, a catheter and nanoparticle deposits. Secondly, an estimate of the temperature distribution in the denoted areas on the basis of field strength and therapy time is shown. This is particularly important for areas which can be treated only to a restricted degree, such as in the head on a frontobasal basis in the area of the optic chiasma (hypothalamus), the sylvian fissure, in which the vascular tree of the middle cerebral artery runs, the corpus callosum or the brain stem.

The data that are input and the simulations that are produced can be stored and printed, and various scenes can be produced per patient. The simulation tool thus provides assistance for the doctor or user in preparing the therapy plan. By way of example, the therapy plan is released by a signature from the doctor who is responsible on the printed therapy proposal. The simulation results presented in the therapy proposal can be used for orientation purposes and do not need to make any particular demands on accuracy.

The simulation software can be operated on a customer's own hardware, and appropriate minimum requirements need to be met. The ambient conditions correspond to those of an environment for the application of medical software.

Overview of the First Exemplary Embodiment

As a program package, the software comprises a "temperature simulator" (subsequently also called "simulator" for short). Following the introduction of magnetic fluid into a tumor, the simulator allows simulation of the temperature distribution in the body area on the basis of the magnetic field strength of the therapy appliance (applicator). The simulator calculates a particular field strength as part of a nonbinding recommendation. To perform the therapy, it is additionally possible to take temperature measurements during the therapy, as a result of which simulation results and temperature measurements together can form the basis for assessment of the therapy by the doctor, said temperature measurements preferably being influential. Naturally, the simulation results are neither a prerequisite for therapy being able to be performed nor binding for performance.

FIG. 1 shows the main steps of a program cycle. The "simulator" program package is called in a main step "temperature simulation". The following main tasks are performed by the simulator:
  Simulation of the three-dimensional temperature distribution which probably results from the application of the magnetic field to superparamagnetic or ferrimagnetic nanoparticles, for example, on the assumption of a simplified physical model (this is described more precisely below); and
  estimation of the H field strength, for example on the basis of particular temperature selections for the patient model.

The simulator package is not directly part of the core of the simulation software, but rather is linked to the core by means of a firmly defined external I/O interface as part of external SOUP ("Software of Unknown Provenance").

The simulator package comprises three independent simulator programs sim_t, sim_h and sim_hr, which are described in FORTRAN77 (execution programs "sim_t.exe", "sim_h.exe" and "sim_hr.exe"). The order of the calls to the simulator programs and the management of the simulator data are undertaken by the core of the simulation software, in this case called the "main program core". The main program core also manages all other main steps which have been shown in FIG. 1, such as image fusion, segmentation, inter alia. In this first exemplary embodiment, the data interchange between the core and the simulator, including the output of program termination messages, is effected by reading/writing from/to a hard disk directory.

The "Temperature Simulation" Program Main Step in Detail

Figure 2:
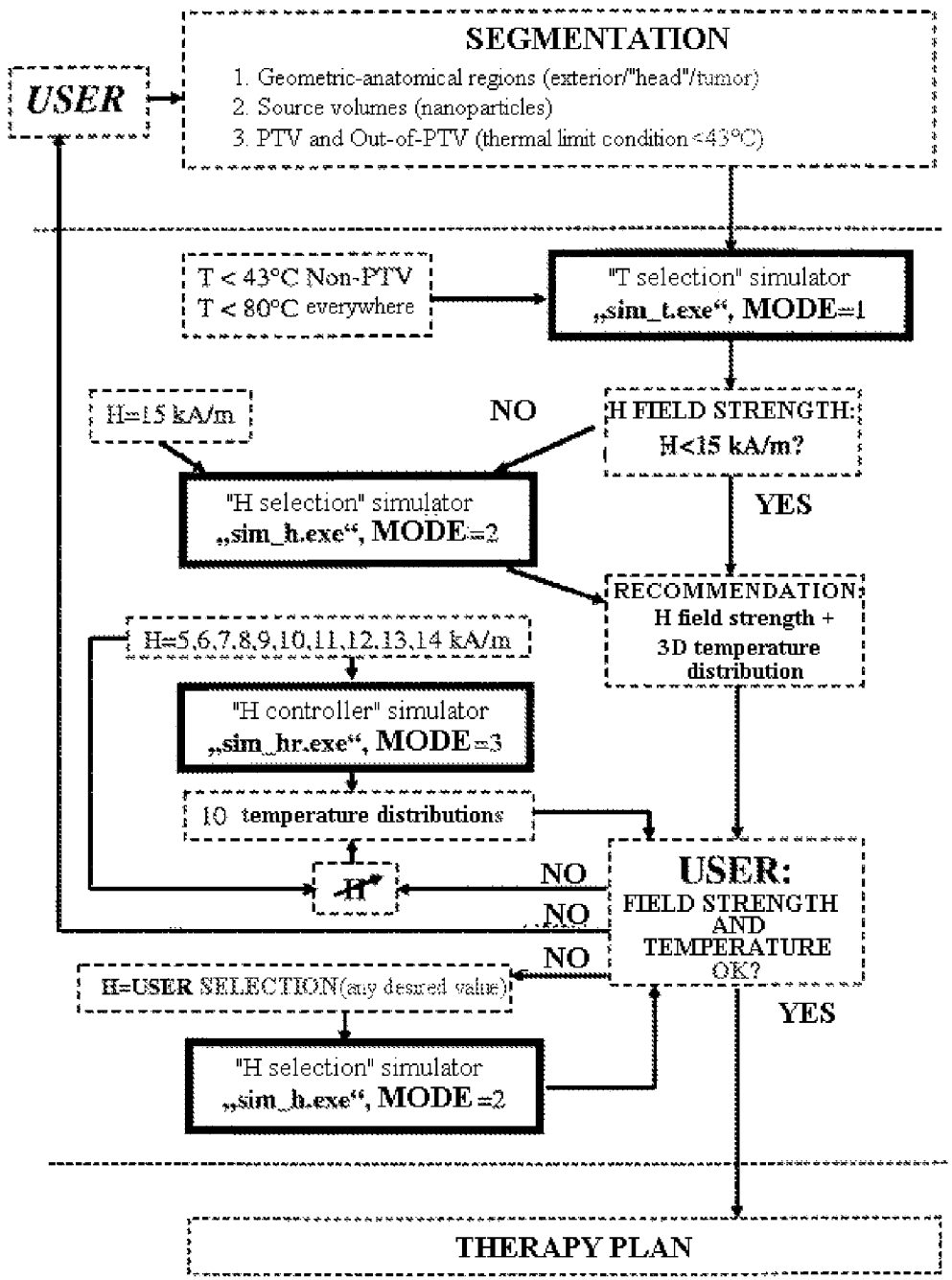
FIG. 2 shows a flowchart for a program cycle from a first exemplary embodiment of an inventive simulator, having a stipulated sequence of calls to the simulator programs.

The time sequence of the calls to the simulator programs in the "temperature simulation" main step is controlled or managed from the main program core and can take place on the basis of a scheme as shown in FIG. 2.

It is stipulated that after a respective change of user in the GUI ("Graphical User Interface") upon a change from the segmentation menu to the temperature simulation menu, the T selection program sim_t.exe starts first in this menu (mode=1). This program automatically (i.e. without any input by the user) has the following two limit temperature selections to comply with:
  43° C. maximum outside the PTV ("non-PTV 43° C. limit")
  80° C. maximum everywhere else, i.e. de facto inside the PTV ("whole-body 80° C. limit").

In this case, PTV ("planning target volume") denotes the treatment area/treatment volume, i.e. the volume that is to be treated or to be heated. This can be stipulated by the user in the segmentation main step (the simulation software can, for example on the basis of manually performed tumor contouring, make a proposal for the treatment volume, for example tumor volume plus border, which can be accepted or altered by the user, that is to say can be restricted or expanded, for example). A temperature value of 43° C. is implemented as a threshold temperature, above which damage to the healthy tissue can increasingly occur, which needs to be avoided as far as possible. A temperature value of 80° C. is implemented as a general temperature limit which must not be exceeded throughout the body, that is to say not even in the tumor volume, for example; this simultaneously limits the power absorption by the body as a whole. Of the two limit conditions, the one which occurs at the lower H field strength becomes effective.

However, it should be noted that the limit values of 43° C. and 80° C. are applied to the treatment of tumors in a body volume such as the human head, for example. Hyperthermia treatments relating to other body volumes, such as the prostate area, may be oriented to the observance of other limit values. By way of example, the limit value in the PTV may be 100° C. instead of 80° C. for thermotherapy on a prostate tumor.

Following the execution of sim_t.exe, the simulation software first of all examines internally, i.e. without the user being notified of the values by GUI, what the level of the H field strength value that is output internally as a sim_t output is. If this value is greater than 15 kA/m (kiloamps per meter), a pass of sim_h.exe (mode 2) starts automatically (without the user needing to make any input) with the selection 15 kA/m (H selection), where 15 kA/m is the maximum H field strength value that can be set on the magnetic field applicator.

If the sim_t.exe output value is less than or equal to 15 kA/m, it is not necessary for a sim_h.exe program run to be automatically started, and the next step follows directly.

In this next step, the temperature distribution and the following values are output graphically to the GUI:
  the H field strength recommendation (the output from sim_t.exe or 15 kA/m from the automatic sim_h.exe run); this output is provided in the GUI window; and
  the maximum temperature reached outside the PTV, and also the maximum temperature reached in the treatment area, and also possibly further output variables; this output is provided in a popup window.

There may be cases in which the prescribed temperature of 43° C., for example, outside the PTV is not reached, specifically when the limit condition of 80° C. in the PTV has already been reached at a lower H field strength value.

On the basis of the output of the initial result as described above, the user can prompt the "H controller" or field strength controller sim_hr.exe (mode=3) to be started (in other exemplary embodiments, the field strength controller can also be started automatically). The system performs these calculations in the background, so that the user has the opportunity to look at the initially ascertained temperature distribution in the meantime. Optionally, the user can skip the start of the H controller, or can terminate the calculation in due fashion.

In the configuration example described here, the H controller calculates ten temperature distributions for the following fixed values of the H field strength (multiple H selection): 5 kA/m, 6 kA/m, 7 kA/m, 8 kA/m, 9 kA/m, 10 kA/m, 11 kA/m, 12 kA/m, 13 kA/m and 14 kA/m. This covers the entire range of settings for the applicator used in this example in steps of 1 kA/m. When the pass has taken place, the user is provided with the opportunity to look at the temperature distributions for these H field strength values by means of the setting of a position on the relevant bar.

The indicated list of H field strength values relates to the treatment of glioblastomas in the head, for example. Other values can be prescribed for treatments in other body areas or volumes. By way of example, for the treatment of prostate tumors, a step size of just 0.5 kA/m can be prescribed for values between 2 kA/m, 2.5 kA/m, . . . , 8 kA/m.

The H controller has no kind of limits for the temperatures reached (other than sim_t.exe in the initial run). Therefore, there may be cases in which the temperatures reached are higher (or lower) than 80° C. in the calculation area and/or higher (and/or lower) than 43° C. outside PTV.

If the user wishes to obtain yet a further review besides the field strength recommendation of sim_t.exe and possibly the ten results for the H controller, he has the option of manually typing the desired input H field strength value in a GUI window. The calculation then starts in the H selection mode (sim_h.exe). He can repeat this as desired.

In the H selection mode, there are no kind of limits in respect of the temperatures reached (other than sim_t.exe in the initial run). Therefore, there may be cases in which the temperatures reached are higher (or lower) than 80° C. in the calculation or treatment area and/or higher (and/or lower) than 43° C. outside the PTV.

Furthermore, the user can return to the segmentation step at any time in order to make corrections on the PTV or other segmentation corrections. In this case, the simulator changes to the initial state. As soon as a new segmented data record (what is known as a "labeled volume" or LV data record, see below) is available and the user changes from the segmentation step to the temperature calculation menu, the whole procedure is repeated, i.e. the simulator starts with the sim_t.exe initial run.

General Technical Approach

The production of the temperature rise by nanoparticles in the magnetic field is notionally split into two steps:
1. In a first step, the nanoparticles in the magnetic field prompt a local power absorption, indicated by a power absorption density ($W/m^3$) or rate (W/kg), in this case denoted generally by SAR ("Specific Absorption Rate");
2. In a second step, this SAR acts as a (main) source of the temperature rise.

The simulation of temperatures which are obtained from values of the H field strength is split into two main steps in the simulator:
1. Ascertainment of an SAR distribution for a given H field strength by what is denoted here as an "SAR solver" (i.e. an appropriate calculation component or a calculation module); and
2. Ascertainment of the temperature distribution ("T distribution") from the SAR distribution (in what is known as the "T solver").

In the SAR solver introduced above, the SAR is determined from metrological data, for example on the basis of a CT (computed tomography) data record with marked magnetic fluid deposits (see below) and a metrologically ascertained dependency of the iron core SAR on the H field strength. Physical approximations can be used for implementation, as are presented in Gneveckow et al. 2004, for example.

In the T solver, a time-dependent BHTE is numerically solved using finite differences by taking account of particular circumstances of the application with magnetic fluids. The T solver can use explicit temperature gradients, as are described in Nadobny et al. 2007, appendix, for example.

In the simulator package, the SAR solver and the T solver do not form separate program units, but rather are merged to form a joint program, with the SAR and T solver components being "mixed" in different ways among one another in the program cycle depending on the selection mode. This is described more precisely below.

The geometric shape of the SAR distribution (and consequently of the temperature distribution) is highly dependent on the geometric positions of the nanoparticles or deposits of the magnetic fluid ("nanodeposits", "deposit volumes") which are latched in the tissue. These nanoparticle positions need to be communicated to the simulator as an input in order to determine the SAR. To this end, a segmented (e.g. binary) three-dimensional data record (in this case denoted as "LV.raw", LV standing for "labeled volume", see below) with marked nanoparticles which is produced on the basis of the planning CT needs to be made available to the simulator in the preceding main step "segmentation". Furthermore, the values of the Hounsfield units at the locations of the nanoparticles need to be known. This is accomplished by reading in the binary CT file CT.raw.

The power absorption of the nanoparticles in the magnetic field can be represented in the simulator in different ways. A specific power absorption can be quantified by a power absorption rate ("Specific Absorption Rate", SAR) in units of watts per kilogram or gram (W/kg or W/g), the mass which needs to be set in this case being the magnetically effective mass, that is to say the mass of the magnetic fluid (in this case the SAR is usually indicated in W/kg) or the iron mass in the case of nanoparticles with an iron core (in this case the SAR is usually indicated in W/g), for example. Instead of using a rate, a specific power absorption can also be indicated via a power absorption density in units of watts per cubic meter or cubic centimeter ($W/m^3$ or $W/cm^3$). If a specific power absorption density is involved, the volume would be approximately the volume of the magnetic fluid.

A specific reference power absorption rate or density can relate to the (measured) power absorption of a magnetic fluid with a carrier (for example water) and the nanoparticles "dissolved" therein, for example. In this case, the quantity of the nanoparticles in the carrier is known extremely precisely for such a reference measurement (e.g. in molar mass). The reference statement thus relates to a magnetic fluid in the reference state prior to instillation. The iron core SAR "SAR_fe" used here is one such reference statement which is usually based on the iron mass and is indicated in W/g.

The actual power absorption ("Absorbed Power Rate" or "Absorbed Power Density", APD, in $W/m^3$) in the tissue is dependent on the density of the magnetically effective (masses of the) nanoparticles which is present in said tissue. Hence, the actual or tissue-specific power absorption in the tissue is altered in comparison with the specific reference power absorption in this manner on the basis of density; in general, the nanoparticles in the tissue are present in a lower density than the reference magnetic fluid (they are "diluted"). In order to limit the amount of terms used, the use of APD should be avoided. Even for the actual power absorption, we therefore continue to refer to the SAR or a spatial SAR distribution SAR (x,y,z), for example, even if, strictly speaking, the unit $W/m^3$ should be used. The language use is justified insofar as the conversion from SAR to APD or vice versa is a simple matter for the simulator: the actual density of the (iron mass of the) nanoparticles per voxel is known, being derived from the CT data (e.g. grayscale values in HU). The (specific/actual) power absorption rate and power absorption density can also each be converted into one another by a density factor (magnetically effective mass density in the magnetic fluid/in the tissue following instillation). In this sense, we also refer to a volume SAR in this case. Hence, the terms "SAR" and "volume SAR" are equivalent to the term power absorption density, and the issue of the form in which the data are kept by the simulator is one of numerical optimization, unlike in the case of the "(reference) power absorption rate", e.g. the SAR_fe, which is based on the mass of the nanoparticles in W/g.

In other words, the term "power absorption density" as used here relates to a (volume) SAR, while the term "(reference) power absorption rate" relates to a reference variable that is determined metrologically outside the body (in vitro), like SAR_fe.

A volume SAR can thus be understood to mean either a power absorption rate in W/kg that is deposited in the body or a power absorption density in units of $W/m^3$ (watts per cubic meter), for example, that is deposited in the body. In addition, a (reference) SAR rate or (reference) power absorption rate is also used which is indicated in units of W/kg (watts per kilogram), W/g (watts per gram), etc., for example.

According to general language use, the supplementary "distribution" is occasionally omitted. A statement may thus be a location-dependent distribution, that is to say SAR (x,y,z), or a location-independent value, for example an average power absorption density such as the volume SAR SAR_aver. Whether or not a distribution is present is evident to a person skilled in the art from the general context.

Re the Functionality of Individual Components or Modules in the First Exemplary Embodiment Depending on the input or selection mode, the simulator execution program "sim_t.exe", "sim_h.exe" or "sim_hr.exe" is called from the main program of the simulation software in a particular order in time. Possible orders have already been discussed above.

The simulator provides two ways or options for ascertaining (simulating) an absolute temperature distribution:
Using the "H selection" ("H" symbolizes H field strength). The absolute value of the field strength H is prescribed (typically in kA/m). The temperature distribution T(x,y,z) (in ° C.) is sought.
Using the "T selection" ("T" stands for temperature). Temperature limit values T_limit (in ° C.) are prescribed, and the field strength value H (in kA/m) and the associated temperature distribution T(x,y,z) (in ° C.) are sought.

The T selection is implemented using the execution program "sim_t.exe", and the H selection is implemented using the execution program sim_h.exe. The third program module, sim_hr.exe, also uses a (multiple) H selection. sim_t.exe and sim_h.exe each calculate one temperature distribution, while ten temperature distributions are ascertained in one cycle for ten values of the H field strength in the case of sim_hr.exe (the "H controller").

A transfer parameter (or input value from the point of view of the simulator) "MODE" having the value MODE=1, the "H selection" (sim_h.exe) MODE=2 and the "H controller" (sim_hr.exe) MODE=3 is assigned to the calculation type "T selection" (sim_t.exe).

The text below provides a more precise description, by way of example, of the three simulator program modules (which can each also be available as standalone programs) with their functionalities.

H Selection (MODE=2, sim_h.exe)

Figure 3:
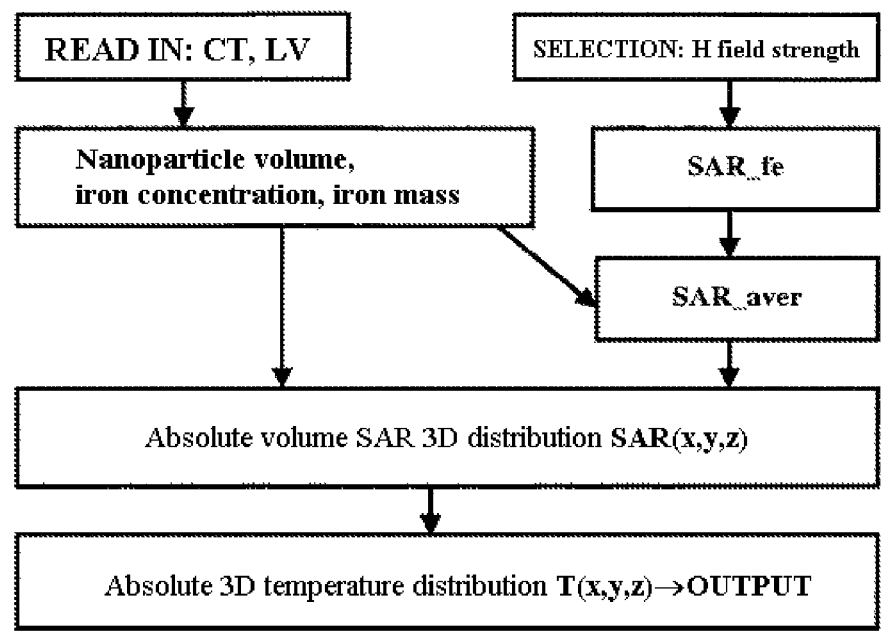
FIG. 3 shows a flowchart for a program cycle from the simulator from FIG. 2 in what is known as mode 2 (execution program "sim_h.exe": selection of the H field strength, "H selection" for short.

A schematic illustration of the cycle of the program module sim_h.exe is shown in FIG. 3. The absolute value of the H field strength H is prescribed. The temperature distribution T(x,y,z) is sought.

First, the nanodeposit volume (deposit volume) or nanoparticle volume ("V_NP") and an average HU value "HU_aver" from all the values HU(x,y,z) in V_NP are formed from the evaluation of the geometric nanoparticle distribution (read in via LV.raw) and comparison of the Hounsfield units ("HU(x,y,z)", read in via CT.raw).

Next, the average iron concentration is estimated from the average "HU_aver", and from this the iron mass "m_fe" (more generally: the particle mass) in the V_NP is estimated, it being assumed in this case that the nanoparticles have an iron core as the magnetically effective component. This approach is thus based on multiple approximations: m_fe is estimated from the average iron concentration, which is in turn estimated from the average HU value. The concentration of the nanoparticles following instillation into the patient is determined from the CT data. Only approximately 50% of the instilled particles remain in the body and are present in the "nanodeposit" in concentrations or distributions which are difficult to foresee.

Independently of this, the simulator derives the iron core SAR "SAR_fe" from the H field strength. This is a reference power absorption rate in units of W/g, for example, based on the iron mass, which indicates a measured power absorption for the nanoparticles in an undiluted reference state, that is to say the power absorption rate of an undiluted magnetic fluid (undiluted batch) containing the nanoparticles prior to instillation into a patient, for example.

The nanoparticles may be magnetic (that is to say ferromagnetic or ferrimagnetic, for example), paramagnetic and/or superparamagnetic. Depending on parameters such as material, size distribution, etc., there may be a mixture of different magnetic properties.

The SAR_fe is calculated by applying a nonlinear characteristic curve SAR_fe=f(H), determined metrologically beforehand for the magnetic fluid. The characteristic curve is determined for a specific applicator and specifically used nanoparticles (magnetic fluid). It is assumed that the treatment area is situated centrally between pole pieces of the applicator (e.g. in an area of <+/−10 centimeters), so that, in a good approximation, the same (maximum) H field strength value can be used everywhere in that area. In order to avoid a complex tabular representation, the characteristic curve SAR_fe=f(H) can be approximated by three fitting factors a,b,c, so that it can assume a form $$SAR\_fe = aH^b + c \quad (1)$$

with the units SAR_fe in W/g (watts per gram) and H in kA/m.

m_fe, SAR_fe and V_NP are now used to estimate an average "SAR_aver" for the volume SAR(x,y,z) based on the tissue mass in W/kg (or, equivalently: multiplied by the specific local density in W/m³ or W/cm³) in the nanodeposit. This is thus an average power absorption density in the deposited state of the nanoparticles.

Next, a location-dependent volume SAR distribution is formed, and the invention assumes with good approximation that in V_NP the SAR values are proportional to the HU values, i.e.

$$SAR(x,y,z) = HU(x,y,z) * SAR\_aver/HU\_aver \text{ in } V\_NP \quad (2),$$

$$SAR(x,y,z) = 0 \text{ outside } V\_NP \quad (3).$$

All the values HU(x,y,z) are positive in V_NP, which means that no physically impossible negative SAR values can arise.

With the location-dependent power absorption "density" distribution SAR(x,y,z) as the source of the temperature, a BHTE T(x,y,z)=f(SAR(x,y,z)) is then numerically solved, e.g. on the basis of Nadobny et al. 2007, equations (1)-(2), and in this case a finite difference method with explicit temperature gradient calculation based on Nadobny et al. 2007, equations (8)-(15), is applied.

The BHTE describing the model is dynamic, i.e. time-dependent. After some time, a steady state condition is reached, in which the supply of heat by power absorption in the applied magnetic field is the same as the heat dissipation for the blood flow, cooling in the environment, perfusion terms. On the basis of experience, such a condition is reached after approximately 20 min. It may be prescribed in the simulator that, taking account of an appropriate safety margin, the steady state condition is meant to be deemed to have been reached after 30 min (minutes), for example (hyperthermia treatment can take between 1 hour and 1.5 hours, for example). In principle, the user may also be treated in the initial phase (before a steady state is reached). The simulator operates in a time domain, and can therefore also model and provide (output) any times before a value of 20 min or 30 min.

The H selection option (sim_h.exe) (MODE=2) requires just a single pass in order to numerically solve the BHTE T(x,y,z)=f(SAR(x,y,z)).

The invention proposes that in the case of the H selection the temperature is not limited, i.e. depending on the level of the H field strength, any temperatures can arise in the body which may also be above the usual temperature limit values (e.g. 43° C. in healthy tissue).

T Selection (MODE=1, sim_t.exe)

Figure 4:
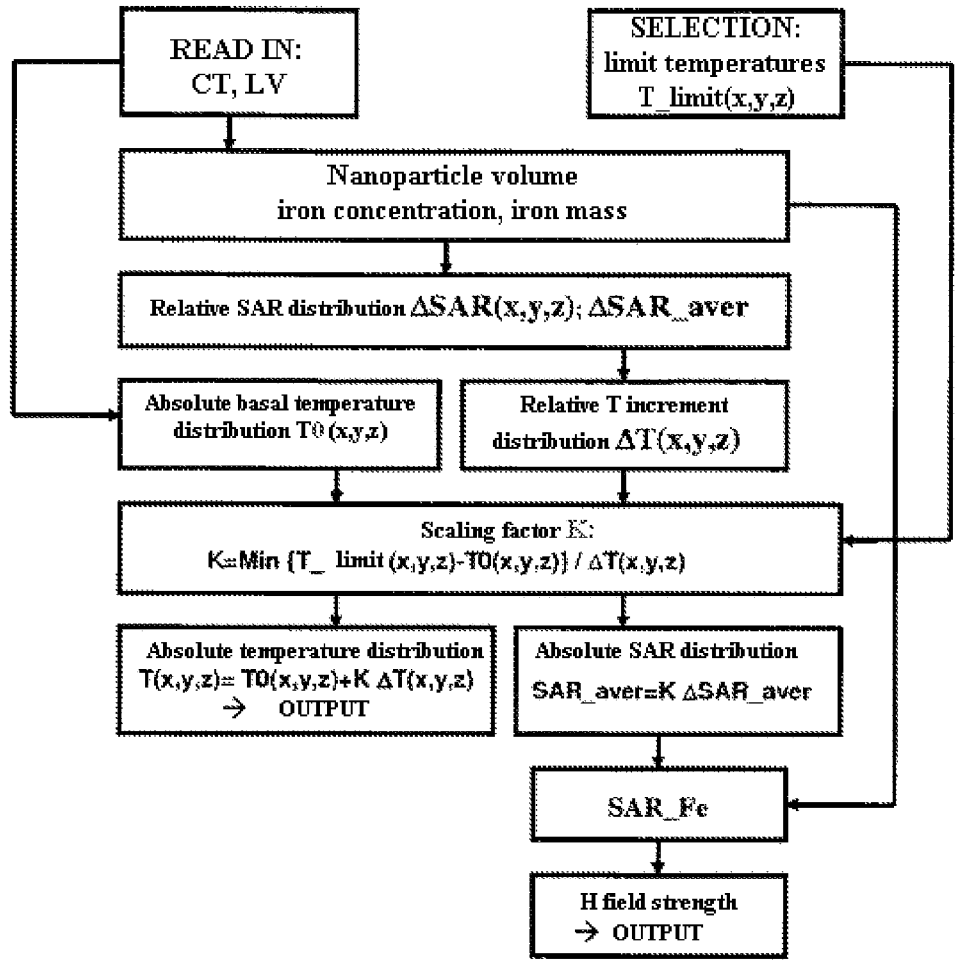
FIG. 4 shows a flowchart for a program cycle from the simulator from FIG. 2 in mode 1 (execution program "sim_t.exe": temperature selection, "T selection" for short)

FIG. 4 schematically shows a program cycle for the simulator in T selection mode. Temperature limit values T_limit (x,y,z) are prescribed, and the field strength value H and the associated temperature distribution T(x,y,z) are sought.

First of all, the nanoparticle distribution is read in from LV.raw and the Hounsfield units are read in via CT.raw—as in the case of sim_h.exe. Next, the iron concentration (generally the magnetically effective particle concentration) is determined and from this the iron mass m_fe (generally the magnetically effective particle mass) is determined, as in the case of sim_h.exe. These variables are independent of an acquired H field strength.

Further progression of sim_t.exe is different than in the case of sim_h.exe, however, since the absolute value of the field strength is not prescribed, but rather is now sought. The procedure comprises the calculation of an appropriate volume SAR (in W/kg, or optionally as a power absorption density in W/m³) which "fits" the prescribed limit temperature, and also finding the H field strength from the calculated volume SAR.

The limit temperature selections T_limit(x,y,z) that need to be observed simultaneously and with equal authorization in the example described here are as follows:

for the "non-PTV region" (for a Boolean operation, "body volume minus PTV"), a maximum admissible temperature value (=temperature limit value) T_limit(non-PTV) is prescribed. By way of example, this value may have been set to 43° C. by default in the main program of the simulation software and transferred to the simulator thus, i.e. T_limit(non-PTV)=43° C. The "non-PTV" region corresponds roughly to the healthy tissue or the tissue that is not to be treated.

The temperature everywhere in the body volume is meant to be no more than 80° C. This value may have been stipulated internally in the simulator, for example. In interaction with the above limit value, on the basis of which the non-PTV is meant to be at no more than 43° C., this is a limit for the treatment area PTV, and therefore T_limit(PTV)=80° C.

The resultant field strength H must observe both selections, i.e. it is meant to be low enough for all the temperatures T(x,y,z) to be less than or equal to 80° C. in the PTV and at the same time less than or equal to 43° C. outside the PTV. In other words, of two field strength values which each observe one of the two T selections, the lower is output.

To observe these T selections, it would theoretically be possible to start sim_h.exe multiple times and to recurrently readjust the input field strength, so that the T selections would be observed at the end of such an iterative process. This iterative and accordingly imprecise and complex path (cf. "iterative way" in Nadobny et al. 2007, page 1841) is not pursued in this case.

The procedure according to the invention is different in this case in order to determine the H field strength value directly, in a resource-saving manner and nevertheless precisely. In this case, it should be borne in mind that the statement of problem is in no way trivial, since the SAR (and hence temperature) is dependent on the H field strength in a nonlinear manner. However, a linear relationship can be indicated at least for some of the statement of problem, specifically between the SAR and the temperature (cf. "decomposition way" in Nadobny et al. 2007, page 1841, equations (5a), (5b), (6)). Thus, the temperature distribution T(x,y,z) is first of all split into a basal component T0(x,y,z), which is obtained without SAR, and into a temperature rise component T_rise(x,y,z)=K*ΔT(x,y,z), with the result that:

$$T(x,y,z) = T0(x,y,z) + K*\Delta T(x,y,z), \quad (4)$$

and for the SAR the following is true $$SAR(x,y,z) = K*\Delta SAR(x,y,z). \quad (5)$$

K is a scalar scaling factor (in MODE=1, we refer to "temperature-based" scaling factor), $\Delta T(x,y,z)$ is the relative temperature increment and $\Delta SAR(x,y,z)$ is the relative SAR distribution, which can also be called the relative power absorption density or is equivalent thereto. Unlike in the case of sim_h.exe, an absolute value SAR_aver is not determined from SAR_fe, but rather an arbitrary (relative) test average "$\Delta SAR\_aver$" for the relative volume SAR $\Delta SAR(x,y,z)$ is prescribed internally. By way of example, this test average may be set as $\Delta SAR\_aver=100$ W/kg in the simulator. In a manner similar to that in equation (2), the invention approximates the location-dependent $\Delta SAR(x,y,z)$ values therefrom as follows:

$$\Delta SAR(x,y,z) = HU(x,y,z) * \Delta SAR\_aver / HU\_aver \text{ in } V\_NP, \quad (6)$$

$$\Delta SAR(x,y,z) = 0 \text{ outside } V\_NP. \quad (7)$$

Next, two passes for numerically solving the BHTE are started in succession: once for $T0(x,y,z)$ (with $SAR(x,y,z)=0$) and once for the relative temperature increment $\Delta T(x,y,z)=f(\Delta SAR(x,y,z))$. Next, the temperature-based scaling factor is found using a minimum search over all support points or voxels $x,y,z$:

$$K = Min(T\_limit(x,y,z) - T0(x,y,z))/\Delta T(x,y,z)), \quad (8)$$

where $T\_limit(x,y,z)=80°$ C. in the non-PTV and $43°$ C. in the PTV.

When the temperature-based scaling factor K has been found, it is immediately possible to indicate the absolute $SAR(x,y,z)$ and $T(x,y,z)$ using equations (5) and (4) without the BHTE needing to be numerically solved once again. For the average of $SAR(x,y,z)$, the following is likewise true:

$$SAR\_aver = K * \Delta SAR\_aver. \quad (9)$$

Next, the invention performs the initial steps from sim_h.exe in inverse order: first, the iron core SAR SAR_fe is determined from the average SAR_aver and the previously determined iron mass m_fe. The last step is the application of a generally nonlinear characteristic curve SAR_fe=f(H) in the inverse sense, i.e. the value SAR_fe is used to ascertain the H field strength value, which is then finally communicated—in addition to the temperature distribution $T(x,y,z)$—to the user as an output.

H Controller (MODE=3, sim_hr.exe)

Figure 5:
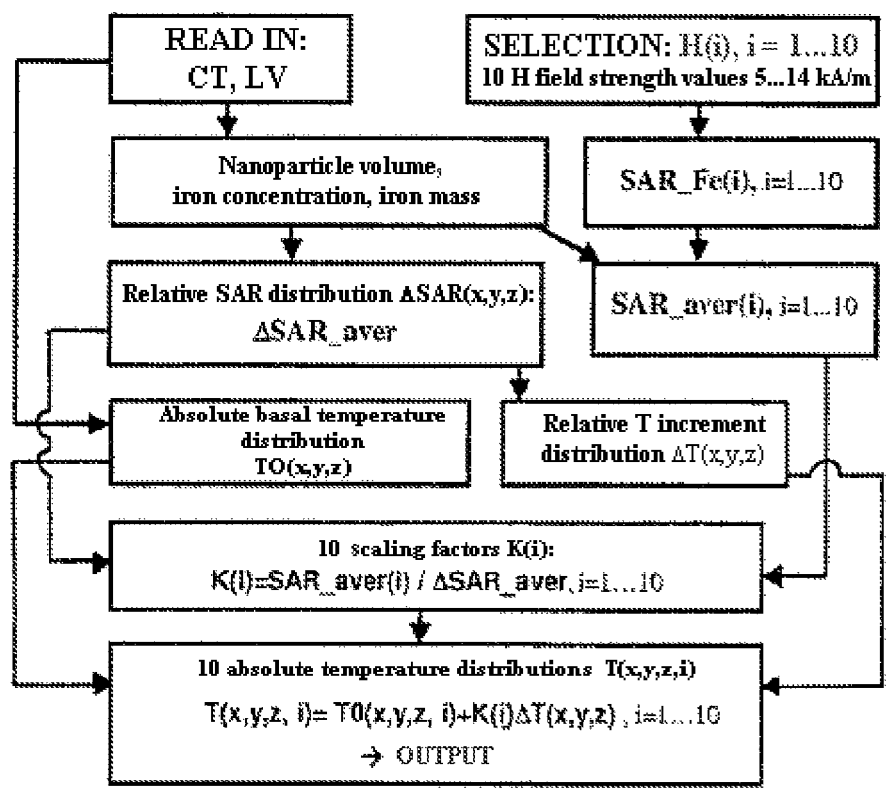
FIG. 5 shows a flowchart for a program cycle from the simulator from FIG. 2 in mode 3 (execution program "sim_hr.exe": what is known as an H field strength controller, "H controller" for short)

FIG. 5 schematically shows a program cycle for the simulator in H regulator mode. In a call, the simulator program sim_hr.exe immediately simulates a plurality of temperature distributions for a multiple H selection, i.e. for different absolute values of H which are made available as input values.

In the example described here, a set of ten temperature distributions is determined for a set of ten firmly prescribed field strength values (5, 6, 7, 8, 9, 10, 11, 12, 13 and 14 kA/m). However, the H controller is not simply a sim_h.exe executed ten times in succession with ten passes for numerically solving the BHTE. In order to save computation time, instead only two passes—in a manner similar to that in sim_t.exe—are required, namely likewise for $T0(x,y,z)$ and $\Delta T(x,y,z)$.

First of all, the evaluation of the geometric nanoparticle distribution (read in via LV.raw) and comparison of the Hounsfield units (read in via CT.raw) are used—in a manner similar to that in the case of sim_h.exe—to determine the average HU value HU_aver, from this the average particle or iron concentration and from this the particle or iron mass m_fe. These values are the same for all H values.

Next, for a relative value of $\Delta SAR\_aver=100$, $\Delta SAR\_aver$ is estimated and $\Delta SAR(x,y,z)$ is approximated—as in sim_t.exe—on the basis of equations (6) and (7) above.

In a manner similar to that in sim_t.exe, two passes are next performed for the purpose of numerically solving the BHTE for $T0(x,y,z)$ and $\Delta T(x,y,z)$.

Next, a loop having i=10 repetitions starts. Each time, the relative H field strength value H(i) is read in, that is to say 5 . . . 14 kA/m in 1 kA/m steps, for example. By applying the characteristic curve SAR_fe=f(H) based on equation (1), the value is used—as in the case of sim_h.exe—each time to calculate the relevant value SAR_fe(i), and this value (and the initially determined iron mass m_fe) is used to estimate the absolute average of the volume SAR, SAR_aver(i).

Hence, for each loop repetition, a scaling factor K(i) can be determined according to the invention from (according to the invention, we refer in MODE=3 to "power-absorption-based" scaling factor):

$$K(i) = SAR\_aver(i) / \Delta SAR\_aver. \quad (10)$$

With the power-absorption-based scaling factor K(i), an absolute temperature distribution is obtained for each i:

$$T(x,y,z,i) = T0(x,y,z) + K(i) * \Delta T(x,y,z), \quad (11)$$

and is then output. Hence, ten absolute (scaled) temperature distributions are output in succession, although only two passes were required for numerically solving the BHTE.

It is pointed out that the power-absorption-based scaling (power-absorption-based scaling factor K as per equation 10) performed in the case of the H controller (MODE=3) is based on the specific power absorption rate (SAR) and is therefore fundamentally different than the scaling which is performed in the T selection (MODE=1) on a (limit) temperature basis (temperature-based scaling factor K as per equation 8). In addition, it is noted that the power-absorption-based scaling factor K, in the case of the H controller (equation 10), cannot simply be formed by forming a ratio of H values, as is explained by the generally present nonlinearity of the characteristic curve SAR_fe=f(H).

Binary Input File CT.Raw

This 3D data record can represent a regular 3D grid, the elements (pixels) of which have associated CT density values (Hounsfield units, as "short" numbers). The geometric reference to the position (x,y,z) of an element in the CT grid is obtained via the x,y,z index and the statements relating to the bounding box which are additionally transferred to the simulator. The x coordinate is the fastest changing (inner loop), and the z coordinate is the slowest (outer loop). The CT data record must correspond to the postoperative planning CT and contain nanoparticles (following instillation of the magnetic fluid). The simulator is interested particularly in the CT values in the nanoparticle pixels. For these values, the simulator derives the information about the current iron concentration (that is present following the instillation in the body), which is relevant to the calculation of the SAR and/or the temperature.

Binary Input File LV.raw

This data record (LV stands for "labeled volume") can likewise represent a regular 3D grid, the elements of which have associated coded labels ("byte" numbers). The geometric reference to the 3D position (x,y,z) of an element in the LV grid is obtained via the index and the statements relating to the bounding box. The bounding box of LV.raw may be identical to that of CT.raw. The data record LV.raw is produced in the previous program main step "Segmentation", for example on the basis of the planning CT. The labels are used to describe/code the following three types of regions:

Geometric-anatomical regions (exterior, "head", tumor): This information is required in order to perform the calculation of the temperature distribution. By way of example, the simulator models the thermal interface between the body and the exterior, and therefore the relevant geometry must be known. It is also expected that the doctor plots the tumor, even though the simulator can also calculate without a segmented tumor. A distinction is drawn between body (part) volumes, that is to say "head", for example, treatment volumes (PTV), that is to say "tumor+border around the tumor", for example, and deposit volumes, that is to say one or more (many) voxels containing nanoparticles. "non-PTV" would thus be "head minus tumor (incl. border)" in the example.

Nanoparticle areas (source volumes): Geometric positions (marked as labels) of the nanoparticles or deposits of the magnetic fluid which are latched to the tissue ("nanodeposits", deposit volumes). These nanoparticle positions need to be communicated to the simulator as an input in order to determine the SAR. The SAR is produced only in the positions of the nanoparticles. The nanoparticle areas can overlap the geometric-anatomical regions and the thermal limit condition regions. The geometric distribution of the nanoparticles inside the deposit volume or the deposit volumes is important for the calculations, for example in the T solver or H controller.

Thermal limit conditions regions: Regions or organs where particular temperatures T_limit(x,y,z) are not meant to be exceeded. By way of example, a distinction is drawn between the treatment area ("PTV", "planning target volume") and the rest of the head for the healthy tissue ("non-PTV region", i.e. region outside the treatment area). The limit condition regions can overlap the geometric-anatomical regions and the nanoparticle areas. As a standard option, the segmentation editor provides the tumor plus a tumor border of 1 cm as PTV.

The coding of LV.raw is implemented such that, for each 8-bit label, 6 bits are used for coding the geometric-anatomical information, and 1 bit is used for coding the nanoparticles (YES/NO) and the PTV (YES/NO), respectively.

A second exemplary embodiment of the inventive simulation tool is described more precisely below. A program package implements a temperature simulator (occasionally also called just "simulator" below) which is part of a piece of simulation software which has been developed with the aim of providing assistance in cancer therapies. Like the first exemplary embodiment described above, the second exemplary embodiment is also provided for simulations in the head area.

As a result of the introduction of the magnetic fluid into the tumor area ("instillation" or "implantation"), what are known as "nanoparticle deposits" or "nanodeposits" can be found in this area. During the therapy, these nanoparticles can be activated by means of high-level low-frequency external magnetic fields, i.e. the influence of the magnetic field can result in a local temperature rise. On the basis of the CT data, the simulator produces a simulation (protection) of the temperature distribution in the head area on the basis of the magnetic field strength of the therapy appliance (magnetic field activator). This occurs after the instillation but before the therapy. The results provided by the simulator are neither a prerequisite for therapy being able to be performed nor binding for the performance of said therapy, for example in relation to a particular application field strength calculated by the simulator. By way of example, the performance of the therapy can be influenced by a temperature measurement carried out during the therapy. This temperature measurement is more crucial in nature for the doctor than simulation results. Simulation results and—crucially—temperature measurement can provide the doctor with pointers for assessing the therapy.

In a manner similar to that in the first exemplary embodiment, the simulator performs the following main tasks, inter alia:
simulation of a three-dimensional temperature distribution, as is probably obtained through the application of the magnetic field to nanoparticles on the assumption of a simplified physical model;
estimation of a magnetic field strength (H field strength) on the basis of particular temperature selections for the patient model.

In a manner similar to that in the first exemplary embodiment, the simulator is not part of a main program core in this case, but rather is linked to the main program core as part of an external SOUP ("Software of Unknown Provenance"). However, the data interchange between the simulator and the main program core no longer takes place via an external rigid directory interface (complete writing out and reading in of the data via hard disk), but rather the simulator is linked as a program library and therefore the data interchange takes place via main memory. Important changes which arise as a result of this different software structure or architecture include:
linking of the simulator as a program library instead of execution programs such as sim_t.exe, sim_h.exe and sim_hr.exe;
introduction of the "fast H controller" instead of the "H controller";
dynamic memory location management for the FORTRAN arrays.

The modification of the H controller is described in detail further below. Furthermore, the linking as a program library will now be dealt with briefly.

In the case of the first exemplary embodiment, the simulator comprised three separate FORTRAN execution programs "sim_t.exe", "sim_h.exe" and "sim_hr.exe", and each program was responsible for a particular selection mode (modes 1, 2 and 3). Accordingly, a transfer parameter (or input value from the point of view of the simulator) "MODE" with the value MODE=1 was transferred to the calculation type "T selection" ("T" for "temperature"; sim_t.exe program), MODE=2 was transferred to the "H selection" ("H" stands for "magnetic", i.e. selection of an H field strength; sim_h.exe program), and MODE=3 was assigned to the "H controller" (multiple desired field strength values, sim_hr.exe program).

In the second exemplary embodiment which is discussed here, the basic split of the program into three modes is retained (MODE=1, MODE=2 and MODE=3), with MODE=3 having been modified in terms of software (cf. further below). However, the simulator no longer comprises three separate exe programs, but rather acts as a program library. Hence, the communication or the data interchange between the main program core and the simulator no longer takes place via external directory interfaces, but rather takes place via main memory. Advantages of this solution are, inter alia, that it is no longer necessary for large volumes of data to be read out and in via external directories (i.e. from or to a hard disk), and thus the program execution speeds are increased and/or possible sources of error are eliminated.

The simulator implemented as a program library can be called from the main program core. The main program of the program library forms an interface to the main program core, that is to say takes on the tasks of the external interface in the first exemplary embodiment—which interface ensures the provision of CT.raw, LV.raw in said embodiment—at the "SOUP end".

All the main programs in the first exemplary embodiment, i.e. sim_t.exe (for MODE=1, T selection), sim_h.exe (for MODE=2, H selection) and sim_hr.exe (for MODE=3, H controller), are provided as FORTRAN (main) subroutines in the second exemplary embodiment which are then all called sequentially (depending on the MODE) by the main program. These customized main subroutines are referred to here as "mainsubroutines". The order in which the simulator modes are called and the simulator data are managed continues to be controlled and managed from the main program core.

The following main subroutines exist:
"mainsubroutine_sim_t_voxel_win" (for MODE=1, T selection),
"mainsubroutine_sim_h_voxel_win" (for MODE=2, H selection), and
"mainsubroutine_sim_hr_voxel_win" (for MODE=3, fast H controller).

The CT data and the segmented label data are not, as in the first exemplary embodiment, written to the hard disk by the main program core as binary data records CT.raw (CT data record) and LV.raw (data record with coded labels) and then read in by the hard disk again as a binary input for the simulator. Instead, these data are in this case transferred as arrays in the main memory via the simulator.

A text file SimInput.txt (this provides the input for the first exemplary embodiment of the simulator) is not needed in this case. All the input parameters are carried in argument lists from the main program core to the main program of the simulator and on to the three mainsubroutines. This relates to the following input parameters, inter alia: MODE (1,2,3), desired H field strength (H=magnetic field strength, indicated in kA/m), desired maximum temperature in the non-PTV area, molarity and fitting factors a,b,c (profile of the characteristic curve SAR_fe=f(H)), all the CT file dimension parameters (number of elements, bounding box, statements relating to the coordinate system used (m, cm, mm), number of regions).

There are also no output temperature data records written from the simulator to the hard disk and then read into the main program core again in this case. Instead, appropriate arrays are transferred from the main program of the simulator to the main program core via main memory.

All the output parameters calculated in the first exemplary embodiment of the simulation program and then written to the output file SimOutput.txt are in this case transferred from the simulation program via argument lists from the mainsubroutines to the main program of the simulator and on to the main program core via main memory. The most important output parameters are: MODE (1,2,3), resultant H field strength, resultant maximum temperature in the non-PTV area, resultant maximum temperature in the PTV area, percentage share tumor with resultant temperatures>39 degrees, nanoparticle volume, tumor volume, resultant average volume SAR, resultant average Hounsfield unit value in the nanoparticle volume, average iron core SAR.

The following additional parameters are transferred in the argument lists of the mainsubroutines to the main program of the simulator: error messages, and parameters which monitor the order of the calls to the mainsubroutines (MODE=3 must not be called before MODE=1, see below).

Overview of the Cycles in the Second Exemplary Embodiment

The simulator provides the user with two options for ascertaining the absolute temperature distribution:

by means of the H selection: The absolute value of the H field strength is prescribed (in kA/m); the temperature distribution T(x,y,z) (in ° C.) is sought; and by means of the T selection: the temperature limit values T_limit are prescribed (in ° C.), and the field strength value H (in kA/m) and the associated temperature distribution T(x,y,z) (in ° C.) are sought.

The T selection (MODE=1) is implemented by means of the call to the mainsubroutine mainsubroutine_sim_t_voxel_win. The H selection (MODE=2) requires the other mainsubroutine mainsubroutine_sim_h_voxel_win to be called. The fast H controller (MODE=3), which is also an H selection in principle, is implemented by means of the call to the mainsubroutine mainsubroutine_sim_hr_voxel_win, but requires at least one call to mainsubroutine_sim_t_voxel_win beforehand, since it uses the output from mainsubroutine_sim_t_voxel_win as input.

Figure 6:
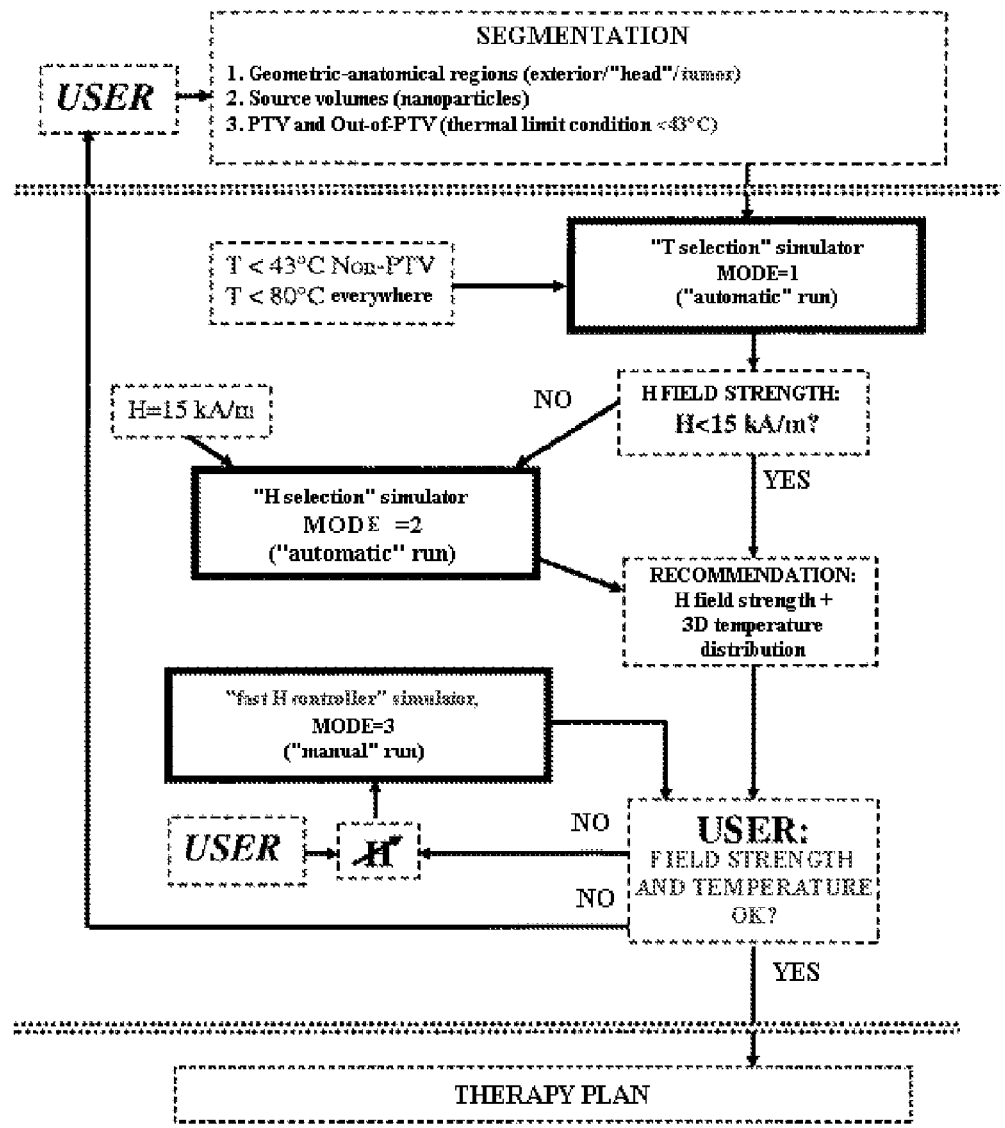
FIG. 6 shows a flowchart for a program cycle from a second exemplary embodiment of an inventive simulator, having a stipulated sequence of calls to the simulator main subroutines.

The chronological sequence of the calls to the simulator programs is controlled or managed from the main program core and is effected on the basis of a fixed scheme, which is shown in FIG. 6.

It is imperatively stipulated that after a changeover from the GUI segmentation editor to the GUI temperature simulation editor, the MODE=1 is always automatically started first, i.e. the T selection subroutine mainsubroutine_sim_t_voxel_win, i.e. without this requiring or needing an input by the user. This program observes two fixed limit temperature selections:
maximum 43° C. outside the PTV ("non-PTV 43° C. limit"), and
maximum 80° C. everywhere else, i.e. de facto inside the PTV ("whole-body 80° C. limit").

In relation to the non-PTV 43° C. limit, it is noted that this value is regarded as a threshold temperature, above which damage to the healthy tissue can increasingly occur. The whole-body limit of 80° C. can also be chosen differently, for example a value in the range between 50° C. and below 100° C., preferably between 60° C. and 90° C., can be chosen. Of the two limit conditions, the one which occurs at the lower H field strength becomes effective.

After the performance of the first, i.e. automatic, pass in MODE=1, the main program core examines internally (without an output being provided by means of GUI) what the level of the H field strength value that is output internally as an output from the main program of the simulator program library is. If this value is greater than 15 kA/m, a pass in MODE=2 again starts automatically with the H selection 15 kA/m, or generally the physically maximum settable H field strength value on the magnetic field activator. If the output value from MODE=1 is less than or equal to 15 kA/m, it is not necessary for a program run to be started in MODE=2, and the next step follows directly.

Following the termination of the automatic passes as described above, the following data are output to the GUI:
temperature distribution;
H field strength recommendation, i.e.
the output from MODE=1 when H<15 kA/m, or
the value 15 kA/m (limiting pass in MODE=2 was performed),
maximum temperature reached outside PTV, maximum temperature reached in the whole calculation area, and further variables.

There may be cases in which the maximum temperature outside the PTV is lower than the maximum admissible temperature (e.g. 43° C.), specifically when the limit condition of, by way of example, 80° C. has been reached in the PTV.

After considering this initial result (the result from the automatic passes) on the monitor, the user decides whether he is satisfied with the result. If this is not the case, he can type in any desired H field strength value and start a fast calculation of the temperature distribution in MODE=3 (fast H controller) for this value as often as desired.

The fast H controller has no limitations at all in respect of the temperatures reached, unlike the T selection in the initial pass. Therefore, there may be cases in which the temperatures reached are higher (or lower) than 80° C. in the calculation area and/or higher (and/or lower) than 43° C. outside PTV.

The user can return to the program main step "segmentation" at any time in order to make segmentation corrections, such as corrections on the PTV. In this case, the simulator changes to the initial state. As soon as there are new LV data present as the output for the segmentation and the user changes from the program main step "segmentation" to the temperature calculation editor, the procedure described above is repeated, i.e. the simulator starts with the initial pass "T selection", etc. Alternatively, the initial pass in MODE=1 can be initiated without returning to the segmentation editor by using a GUI button "Restart automatic temperature simulation". In this case too, the procedure in which the simulator starts with the initial pass "T selection", etc., is repeated.

The three simulator modes are described below according to their aims and functions.

MODE=2 (H selection, Call Goes to Mainsubroutine_sim_h_voxel_win)

Figure 7:
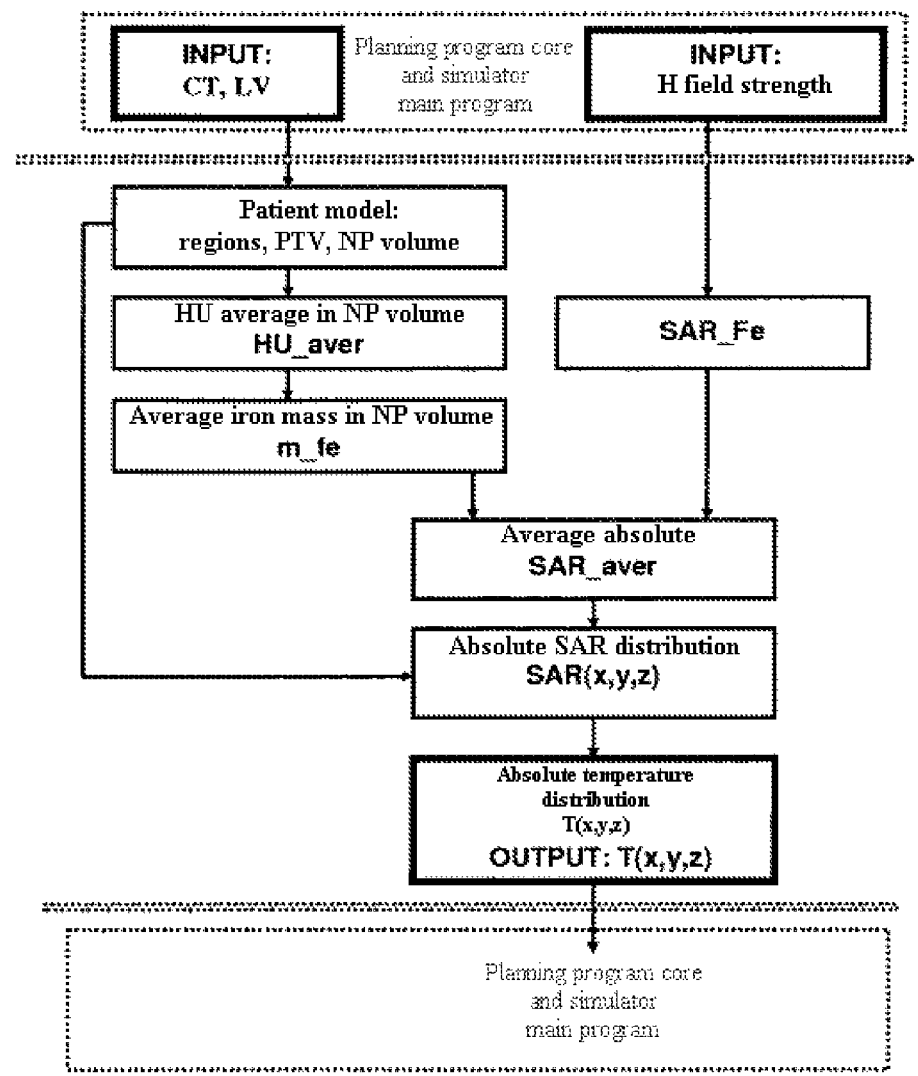
FIG. 7 shows a flowchart for a program cycle from one of the three main subroutines of the simulator from FIG. 6 in mode 2, namely "mainsubroutine_sim_h_voxel_win" (H selection)

The absolute value of the H field strength is prescribed. The temperature distribution T(x,y,z) is sought, cf. the cycle shown schematically in FIG. 7. First of all, the patient model is generated. This is based on the combination of two data records (arrays):

CT data record (array), which is read in by the simulation program as part of patient data that are to be read in (in this regard cf. FIG. 3; in this fundamental cycle, the first and second exemplary embodiments are very similar);

LV data record (array) ("LV" stands for "labeled volume"), i.e. a coded label array, which is produced by the simulation program during segmentation (cf. FIG. 3).

The basis used for the patient model is the LV elements ("labels"), in which the following information is coded on a voxel basis:

the geometric-anatomical regions ("head", "tumor", etc.);
the thermally relevant regions (treatment area, also called PTV, "planning target volume");
geometric distribution of the nanoparticles (NP).

The evaluation of the NP distribution results in the ascertainment of the NP volume V_NP. The comparison with the CT data record then takes place, with the average Hounsfield unit (HU) value "HU_aver" being determined by forming an average for those values of HU(x,y,z) which fall into the V_NP.

Next, the average HU_aver is used to estimate the average iron concentration, and for this the average iron mass m_fe in the V_NP.

Independently, e.g. in parallel with these steps, the simulator derives the iron core SAR ("SAR_fe") from the H field strength. This is accomplished by applying a generally non-linear characteristic curve SAR_fe=f(H) that has been determined experimentally for the magnetic fluid used. In this case, it is assumed that the treatment area is situated centrally between the pole pieces of the magnetic field applicator, where there is the same (maximum, constant) H field strength to a good approximation. In order to avoid a complex tabular illustration, the characteristic curve SAR_fe=f(H) can be approximated by three fitting factors a,b,c as follows, for example:

$$\text{SAR\_fe} = aH^b + c \quad (12)$$

with SAR_fe in W/g (watts per gram) and H in kA/m (kiloamps per meter).

m_fe, SAR_fe and V_NP are now used to estimate the average "SAR_aver" of the volume SAR(x,y,z) in the nanodeposit, cf. equation (2) in Gneveckow et al. 2004, for example.

Next, the location-dependent volume SAR distribution is formed, it being assumed that in V_NP the SAR values are proportional to the HU values, i.e.

$$\text{SAR}(x,y,z) = \text{HU}(x,y,z) * \text{SAR\_aver}/\text{HU\_aver in V\_NP} \quad (13)$$

$$\text{SAR}(x,y,z) = 0 \text{ outside V\_NP}. \quad (14)$$

All values HU(x,y,z) are meant to be positive in V_NP so that no physically impossible negative SAR values occur. This can be ensured as early as in the segmentation editor, for example, by means of appropriate filtering or threshold setting and can possibly be checked again in the simulator.

With the location-dependent SAR(x,y,z) as the source of the temperature, the BHTE T(x,y,z)=f(SAR(x,y,z)) is then numerically solved, cf. Nadobny et al. 2007, equations (1)-(2). This can be solved by using a finite difference method with explicit temperature gradient calculation, as described in Nadobny et al. 2007, equations (8)-(15), for example.

Unlike in MODE=1 and MODE=3, MODE=2 the BHTE describing the model is solved for absolute values of the SAR which are derived from the absolute H selection value. The H selection option MODE=2 therefore requires—unlike in MODE=1 and MODE=3—just a single pass for numerically solving the BHTE T(x,y,z)=f(SAR(x,y,z)).

In the case of the H selection, the temperature is not limited, i.e. depending on the H field strength it is possible for any temperatures to arise in the body, which are also above the usual temperature limit values (e.g. 43° C. in healthy tissue).

MODE=1 (T Selection, Call Goes to: mainsubroutine_sim_t_voxel_win)

Figure 8:
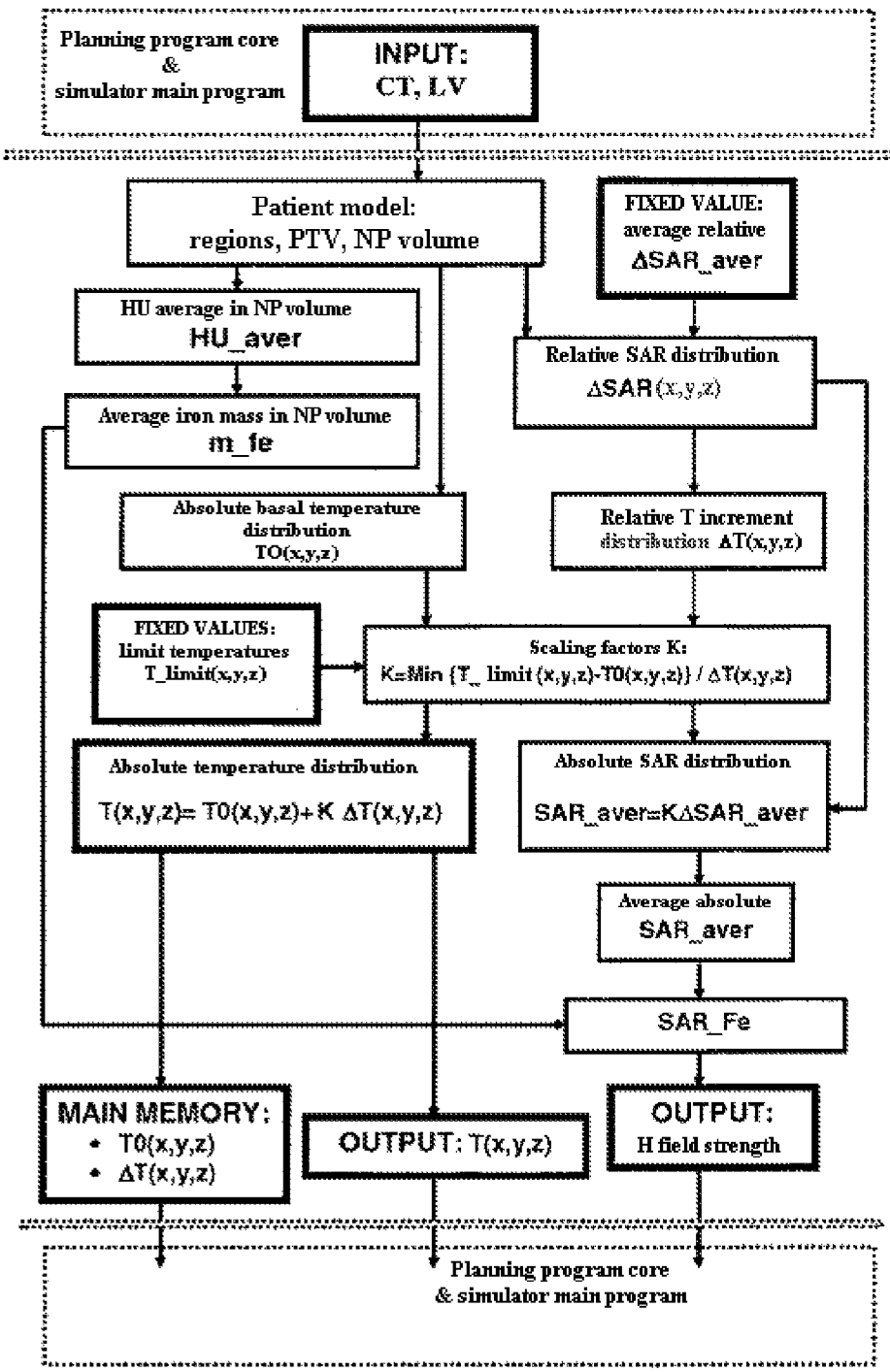
FIG. 8 shows a flowchart for a program cycle from one of the three main subroutines of the simulator from FIG. 6 in mode 1, namely "mainsubroutine_sim_t_voxel_win" (T selection)

Temperature limit values T_limit(x,y,z) are prescribed, and the field strength value H and the associated temperature distribution T(x,y,z) are sought, cf. the schematic illustration in FIG. 8. In contrast to the T selection in the first exemplary embodiment, particular data records are output for the later call for MODE=3 (fast H controller) and are temporarily provided in the main memory.

First of all, the patient model is produced—as in MODE=2—from the LV and CT data and then HU_aver and m_fe are determined for the NP volume (these variables are independent of the applied H field strength). The remainder of the cycle in MODE=1 is different than in the case of MODE=2, however, since the absolute value of the field strength is not prescribed but rather is sought. A procedure for ascertaining an appropriate volume SAR which corresponds to the prescribed limit temperature also has an additional step added for the application of nanoparticles, namely the calculation of the H field strength from the volume SAR.

The limit temperature selections T_limit(x,y,z) which need to be observed simultaneously and with equal authorization are:

the "non-PTV" region corresponds approximately to the healthy tissue or the tissue that does not need to be treated. For this non-PTV region, which in the Boolean sense is "body minus PTV" or "head minus PTV", a maximum admissible temperature value (=temperature limit value) T_limit(non-PTV) is prescribed. This value may be able to be altered by the user, or else may be firmly prescribed. The value may also have been set to 43° C. by default, i.e. T_limit(non-PTV)=43° C.

The temperature in the body is not meant to exceed a maximum value of 80° C., for example, anywhere. This value may be firmly prescribed in the simulator, for example. Since the non-PTV is meant to be at no more than 43° C. at the same time, the second limitation is effective for the treatment area PTV, i.e. T_limit(PTV)=80° C.

The resultant field strength H must observe both selections, i.e. it is meant to be low enough for all the temperatures T(x,y,z) to be less than or equal to 80° C. in the PTV, and at the same time to be less than or equal to 43° C. outside PTV. Of the two field strength values which each observe one of the two T selections, the lower is output.

To observe these T selections, it would be possible to start MODE=2 multiple times, with the input field strength being repeatedly readjusted, so that the T selections would be observed at the end of such an iterative process. This iterative and accordingly imprecise or complex path (cf. "iterative way" in Nadobny et al. 2007, page 1841) is not pursued in this case.

The procedure according to the invention is different in this case in order to determine the H field strength value directly, in a resource-saving manner and nevertheless precisely. In this case, it should be borne in mind that the statement of problem is in no way trivial, since the SAR (and hence temperature) is dependent on the H field strength in a nonlinear manner. However, a linear relationship can be indicated at least for some of the statement of problem, specifically between the SAR and the temperature (cf. "decomposition way" in Nadobny et al. 2007, page 1841, equations (5a), (5b), (6)). Thus, the temperature distribution T(x,y,z) is first of all split into a basal component T0(x,y,z) (as would be obtained without SAR) and into a temperature rise component T_rise(x,y,z)=K*ΔT(x,y,z), with $$T(x,y,z)=T0(x,y,z)+K*\Delta T(x,y,z), \qquad (15)$$

where the following is true for the SAR:

$$SAR(x,y,z)=K*\Delta SAR(x,y,z). \qquad (16)$$

K is a scalar scaling factor—that needs to be ascertained—(we refer to "temperature-based" scaling factor in MODE=1), ΔT(x,y,z) is the relative temperature increment and ΔSAR(x,y,z) is the relative SAR distribution.

In contrast to the first exemplary embodiment, the output for a mainsubroutine_sim_t_voxel_win comprises not only the actual temperature distribution T(x,y,z) but also distributions T0(x,y,z) and ΔT(x,y,z). These temperature distributions are characterized in detail as follows:

T(x,y,z): Absolute resultant temperature distribution, which corresponds to a particular absolute SAR which is necessary in order to comply with particular constraints, e.g. in MODE=1 the limit temperatures are such constraints. T(x,y,z) is also output in the simulation program in accordance with the first exemplary embodiment. T(x,y,z) belongs to the data which are visualized in the GUI ("graphical user interface") of the simulation program.

T0(x,y,z): Absolute "basal" temperature distribution, as obtained without SAR; initial temperature and basal temperature for numerically solving the time-dependent BHTE are identical as for the solution based on T(x,y,z). This temperature distribution is temporarily stored in the main memory and is then available as an input for the fast H controller.

ΔT(x,y,z): The distribution of the relative temperature rise (=temperature increment), said distribution being obtained for an arbitrary, firmly prescribed and/or user-defined SAR level ("fixed value" in FIG. 8). Since it is not the temperature but rather the temperature increment that is simulated in this case, initial temperature and basal temperature for numerically solving the time-dependent BHTE are equal to zero. This temperature distribution is likewise temporarily stored in the main memory and is then available as an input for the fast H controller.

Unlike in MODE=2, an absolute value SAR_aver is not determined from SAR_fe, but rather an arbitrary (relative) test average "ΔSAR_aver" for the relative volume SAR ΔSAR(x,y,z) is prescribed internally as a "fixed value" (constant, cf. FIG. 8) (in the simulator, this test average is set as "ΔSAR_aver=100 W/kg). In a manner similar to that in equation (13), this is used to approximate the location-dependent ΔSAR(x,y,z) values as follows:

$$\Delta SAR(x,y,z)=HU(x,y,z)*\Delta SAR\_aver/HU\_aver \text{ in } V\_NP, \qquad (17)$$

$$\Delta SAR(x,y,z) \text{ outside } V\_NP \qquad (18)$$

Next, two passes for numerically solving the BHTE are started in succession: once for T0(x,y,z)=f(SAR=0) and once for the relative temperature increment ΔT(x,y,z)=f(ΔSAR(x,y,z)). The scaling factor is then found using a minimum search over all support points (voxels) x,y,z ("temperature-based scaling factor"):

$$K=\text{Min}(T\_limit(x,y,z)-T0(x,y,z))/\Delta T(x,y,z) \qquad (19)$$

with T_limit(x,y,z)=80° C. in Non_PTV and 43° C. in PTV.

When the temperature-based scaling factor K has been found, the absolute SAR (x,y,z) and T(x,y,z) can immediately be specified using equations (16) and (15) without having to numerically solve the BHTE again. For the average of SAR(x,y,z), the following is likewise true:

$$SAR\_aver=K*\Delta SAR\_aver. \qquad (20)$$

The initial steps from MODE=2 are then performed in inverse order: i) the iron core SAR SAR_fe is determined from the average SAR_aver and the previously determined iron mass m_fe; ii) the nonlinear characteristic curve SAR_fe=f(H) (cf. Gneveckow et al. 2004, FIG. 5) is applied in the inverse sense, i.e. the H field strength value is ascertained from the value SAR_fe. Said H field strength value is transferred as an output from mainsubroutine_sim_t_voxel_win to the main program of the program library and on to the main program core or to the GUI. Although the three data records T(x,y,z), T0(x,y,z) and ΔT(x,y,z) form the output of mainsubroutine_sim_t_voxel_win, only T(x,y,z) is passed on to the GUI. T0(x,y,z) and ΔT(x,y,z) are temporarily stored in the main memory in order subsequently to be provided as an input for mainsubroutine_sim_hr_voxel_win in MODE=3.

MODE=3 ("Fast H Controller", Call is Made to mainsubroutine_sim_hr_voxel_win)

Figure 9:
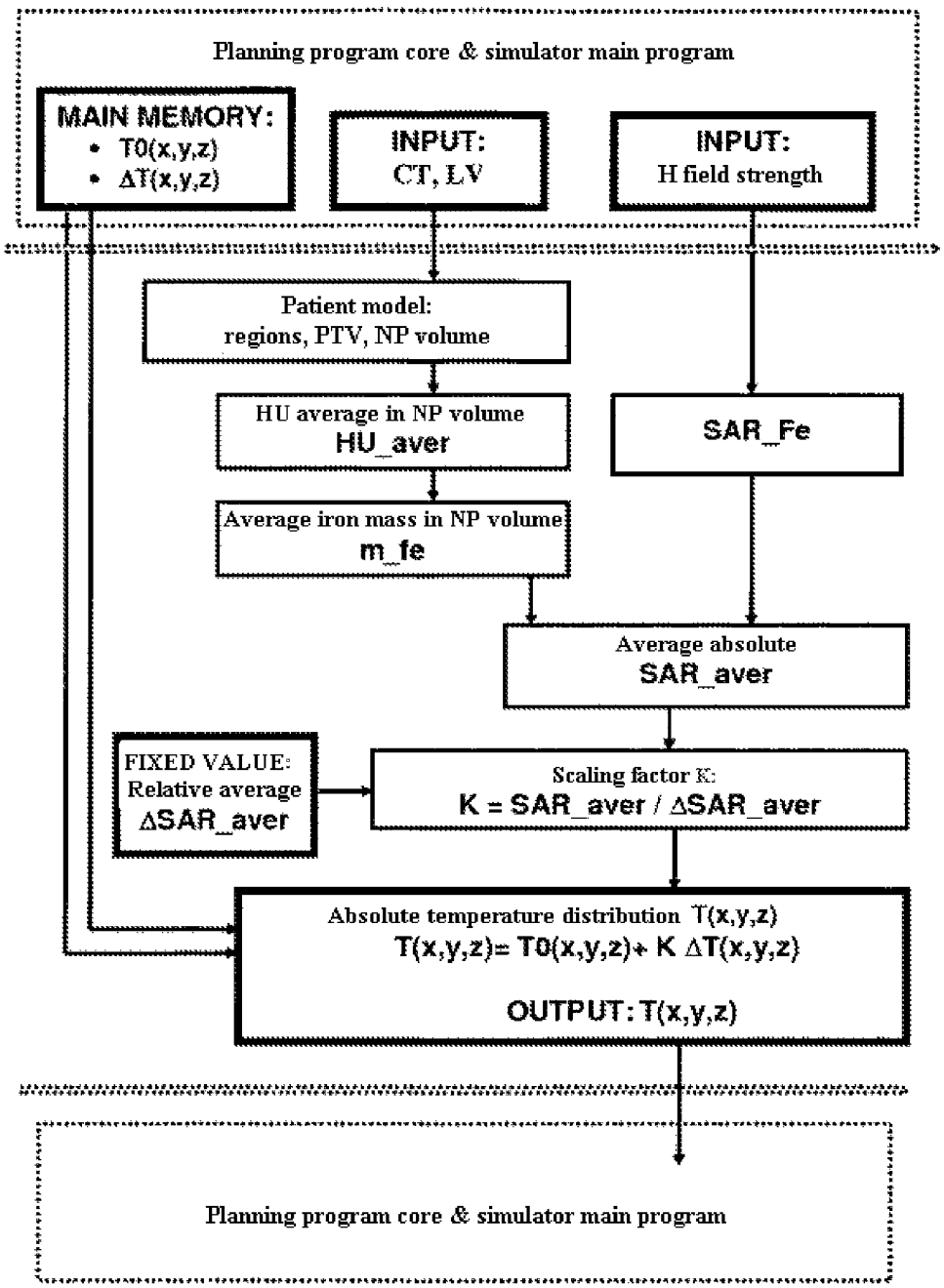
FIG. 9 shows a flowchart for a program cycle from one of the three main subroutines of the simulator from FIG. 6 in mode 3, namely "mainsubroutine_sim_hr_voxel_win" (what is known as a "fast H controller").

In MODE=3, a temperature distribution is ascertained for arbitrary H selection in a matter of seconds without needing to solve the BHTE, for example using a finite difference program. The prerequisite is that T0(x,y,z) and ΔT(x,y,z) are read in as an input for mainsubroutine_sim_hr_voxel_win. These temperature data records should already be present in the main memory, i.e. MODE=1 has already been successfully called and terminated at least once, for example, for a given patient model, cf. FIG. 9.

First of all, the patient model is produced—as in MODE=1 or MODE=2—from the LV and CT data. Next, HU_aver and m_fe are determined for the NP volume.

These variables are independent of the applied H field strength. The average iron mass m_fe has already been calculated in MODE=1 (T selection). As an alternative to recalculation, it is also conceivable for the average iron mass m_fe to be kept in the main memory following calculation in MODE=1 (T selection) for access by MODE=3 (fast H controller). Since the underlying patient model is always the same regardless of the MODE, a calculation such as that for the average iron mass m_fe could also be relocated entirely, for example to the segmentation step (cf. FIG. 1). However, local calculation of such variables may be advantageous, for example in respect of aspects such as a modular structure for the program package, performance of software tests, etc.

Independently of the calculation of the average iron mass, a field strength value H that has been input by the user in the GUI is read in—in a manner similar to that in the case of MODE=2—and the relevant value of the iron core SAR SAR_fe is calculated by applying the characteristic curve SAR_fe=f(H). From this value and from the previously determined iron mass m_fe, the absolute average of the volume SAR, SAR_aver, is then ascertained. At the same time, a relative fixed value of $\Delta$SAR_aver=100 W/kg is prescribed—as in MODE=1—, the fixed value $\Delta$SAR_aver in MODE=3 needing to be identical to the fixed value $\Delta$SAR_aver in MODE=1.

The invention therefore allows the scaling factor K to be determined from (according to the invention, in MODE=3 we refer to the "power-absorption-based" scaling factor):

$$K = \text{SAR\_aver}/\Delta\text{SAR\_aver}. \tag{21}$$

The calculated power-absorption-based scaling factor K and the T0(x,y,z) and $\Delta$T(x,y,z) which have previously been calculated in MODE=1 and are present in the main memory result in the sought temperature distribution T(x,y,z) when equation (15) is applied, said temperature distribution then being output to the GUI. Since the BHTE does not need to be solved in the case of the fast H controller, the method described above is executed by means of a standard processor in a matter of seconds.

It is pointed out that the power-absorption-based scaling performed in the case of the fast H controller (MODE=3) (power-absorption-based scaling factor K as per equation 21) is based on the specific power absorption rate (SAR) and is therefore fundamentally different than the scaling which is performed in the T selection (MODE=1) on a (limit) temperature basis (temperature-based scaling factor K as per equation 19). In addition, it is noted that the power-absorption-based scaling factor K cannot be formed simply by forming a ratio of H values in the case of the fast H controller (equation 21), which is explained by the nonlinearity that is generally present in the characteristic curve SAR_fe=f(H).

The second exemplary embodiment which is described here involves calculation of the basal temperature distribution and the relative temperature increment distribution in MODE=1 (T selection) and provision of said distributions in the main memory as a basis for the fast H controller which is sometimes subsequently called (MODE=3). Other exemplary embodiments are likewise conceivable. By way of example, the two temperature distributions could be calculated and provided in the main memory (only) when the fast H controller is first called. In this case, the simulator would react to the first call to the first H controller more slowly, while the subsequent calls to the fast H controller would then be reacted to very quickly, i.e. virtually without waiting times, with the output of the temperature distribution that results from the input H field strength.

The second exemplary embodiment described here has two program components for calculating a specific temperature distribution on the basis of a prescribed or a user-defined H field strength value, namely once on the H selection (MODE=2) and furthermore on the (fast) H controller. In another exemplary embodiment, it would also be possible for just the (fast) H controller to be provided. However, it is noted that the H selection calculates a specific temperature distribution independently of a basal temperature distribution and a relative temperature increment distribution. The presence of two independent calculation paths in one program package may be advantageous for test purposes, for example, and for maintenance and further development.

One of the two paths of calculation may also be better suited in a specific environment, e.g. a hardware environment, or according to specific requirements. Thus, in one particular exemplary embodiment, the simulator may be of configurable design, for example. An experienced user would set the simulator such that, by way of example, basal temperature distribution and relative temperature increment distribution are not written out in MODE=1 (T selection), so as to save main memory. From his experience and the output from the T selection (MODE=1), the user already favors a particular H value anyway, which means that the resultant, final temperature distribution can be calculated by calling the H selection once. Since the main memory requirement is limited in this case, such a configuration is sometimes suitable for a hardware configuration with accordingly limited resources too.

In yet another variant, the automatic start of the T selection (MODE=1) is dispensed with. Instead, the simulator awaits a user input. If this comprises an appropriate command, the calculation of the T selection can begin, e.g. on the basis of the prescribed temperature limit values. If the user input comprises an H field strength value, the H selection can be started, or the fast H controller (this may in turn be dependent on the available hardware resources). If the latter basal temperature distribution and relative temperature increment distribution are not yet available, they ought to be produced upon the first call.

Interfaces Between Temperature Simulator and Main Program Core

In the first exemplary embodiment, the input values for the simulator were transferred to the simulator via an external text directory interface from main program core. To this end, a text file SimInput.txt was formed which had a particular firmly defined line-based structure. The input values were read from SimInput.txt when the exe programs were called. In the simulator described here (in the second exemplary embodiment), SimInput.txt is no longer in existence and the data are transferred via an internal interface between the main program core and the simulator program library via main memory, i.e. the data are transferred via an internal program interface.

At the simulator end, this interface is implemented by means of argument lists. The simulator input is generated from main program core (for example in C++) and transferred to the FORTRAN simulation library by means of argument lists. By way of example, the input arrays and input parameters comprise:

1-D array with CT data, i.e. HU values;
1-D array with LV data, i.e. the segmented labels;
input parameters in argument lists, comparable with those from the former text file SimInput.txt from the first exemplary embodiment.

The simulator output is generated in the FORTRAN library and transferred to the main program core or the GUI by means of argument lists. By way of example, the output arrays or parameters comprise:

1-D array with the temperature values T(x,y,z); and output parameters in argument lists which may be required in the GUI and for producing a therapy plan (some of these parameters are written to an output file SimOutput.txt in the first exemplary embodiment).

The 3D CT data can be represented in the form of dynamic 1D FORTRAN arrays which can be read into the main program core in the "patient data" step and in the "segmentation" step.

An array can represent the 3D CT data for a regular 3D grid, the elements (pixels) of which have associated CT density values ("Hounsfield units" values, i.e. "HU values"). The geometric reference to the position (x,y,z) of an element in the CT grid is obtained by means of the x,y,z index and the statements relating to the bounding box which are transferred to the simulator in the main memory from the main program core. The CT data record has to correspond to the postoperative planning CT and contain image information about the nanoparticles (following instillation of the magnetic fluid). For the simulator, particularly the HU values in the nanoparticle pixels are of interest. From these values, the simulator derives information about the iron concentration which is present in the body following the instillation. The information is relevant to the calculation of the SAR and then the temperature.

A further array can represent coded "labeled volume" (LV) data (labels) that are generated as a result of the segmentation on the basis of the planning CT. In the geometric service, this array maps a regular 3D grid, the elements of which have associated coded labels (numbers). The geometric reference to the 3D position (x,y,z) of an element in the LV grid is obtained by means of the index and the statements relating to the bounding box. The bounding box of such an LV data record or grid is identical to that of the CT data record. The LV data (labels) are used to describe the following three categories of regions:

geometric-anatomical regions (exterior, "head", "tumor"): This information is required for calculating the temperature distribution. In particular, the thermal interface between the body and the exterior is modeled in the simulator, and therefore its geometry must be known. The tumor should also be represented, although the simulator can compute even without a segmented tumor. In a precise sense, the "head" region means "head minus tumor".

Nanoparticle areas (source volumes): geometric positions (marked as labels) of the nanoparticles ("nanodeposits") latched in the tissue. These nanoparticle positions need to be communicated to the simulator as an input for determining the SAR. The SAR is produced only at the positions of the nanoparticles. The nanoparticle areas can overlap the geometric-anatomical regions and the regions with, for example, thermal limit conditions. If segmented nanoparticle regions are not present, the program is terminated.

Thermal limit condition regions: Regions (e.g. organs) in which particular temperatures T_limit(x,y,z) are not meant to be exceeded. In a second exemplary embodiment, a distinction is drawn just between the treatment area (PTV) and the rest of the head (non-PTV region), i.e. the region outside the treatment area, hence the healthy tissue. The limit condition regions can overlap the geometric-anatomical regions and the nanoparticle areas. As a standard option, the PTV region can be produced in a segmentation editor as a tumor plus a tumor border of a desired width. If the segmented PTV region is not present, the program is terminated.

The coding of the LV data can be implemented in the main step "segmentation" by using, for each element of an 8-bit label, 6 bits for coding the geometric-anatomical information and 1 bit for coding the nanoparticles (YES/NO) and the PTV (YES/NO), respectively.

Re the Differences Between the First and Second Exemplary Embodiments

The first exemplary embodiment, described with reference to FIGS. 2-5, differs from the second exemplary embodiment, described with reference to FIGS. 6-9, in the following aspects, inter alia:

linking of the temperature simulator as a program library ("SOUP integration");

other programming/implementation of the H controller or fast H controller.

In the first exemplary embodiment, the temperature simulator is implemented in the form of separate/autarkic execution programs. In the second exemplary embodiment, the temperature simulator is implemented as a program library. In this case, the temperature simulator programs are not called as separate exe files via an external directory interface, but rather they need to be managed as methods of a program library that is linked to the main program core by using an internal interface that can be actuated directly from the main program core. One of the advantages of this solution is that it is not necessary for large volumes of data to be written to or read in from the hard disk via external directories (as in the case of the first exemplary embodiment). Hence, the comparatively slow hard disk write and read operations are dispensed with, which can raise the execution speed of the simulator. A possible source of error is also eliminated in this manner.

In relation to the operation of the "H controller" in the first exemplary embodiment in contrast to the "fast H controller" of the second exemplary embodiment, it is noted that the simple H controller involves the numerical calculation of two temperature distributions, namely the basal temperature distribution and the relative temperature increment distribution, in a manner similar to that in MODE=1, by solving the BHTE twice. A loop is then called with i=10 passes, for example. For each pass, a predefined H field strength value H(i) serves as an input, so that calculations for a total of 10 H field strength values, e.g. from 5 kA/m to 14 kA/m, are performed in 1 kA/m steps. Each loop pass i=1 . . . 10 involves the determination of a power-absorption-based scaling factor K(i) by which the temperature increment distribution is multiplied. i=10 resultant temperature distributions are obtained, formed on the basis of the scaling scheme described further up. These i=1 . . . 10 temperature distributions are then written in succession to an external hard disk directory. From there, it can be loaded as required by the user.

Behind this approach to a solution, there is the assumption that the ten distributions (i=1 . . . 10) can be calculated in the background (in a manner similar to a batch job), while the user is looking at the temperature distribution ascertained in the first automatic pass (Mode=1) on the screen. This means that the user loses no time and, when he is finished looking at the temperature distribution, has 10 further temperature distributions available which cover the entire H field strength range that can be set. He can therefore change over between these temperature distributions. If he is interested in a specific value which lies between the firmly prescribed H(i) values, he could calculate a pass with Mode=2 (H selection) again for this value.

In the practical application, this requires a comparatively large amount of memory space on the hard disk for large data records, however, in order to store all 10 distributions; a typical value in this case is in the order of magnitude of 2 GBytes. Writing the 10 temperature distributions to the hard disk and reading them from the hard disk takes a correspondingly long time. Sequentially loading the temperature data records from the hard disk is associated with a series of operations, for example loading the contours, calculating a catheter spline, etc., these possibly being comparable with a pass of the BHTE from the point of view of resource consumption. Sometimes, the advantage of changing over between the different previously calculated data records is thus inexhaustible.

The "simple" H controller based on the first exemplary embodiment provides only temperature distributions for firmly predefined H field strengths. If a value between the predefined values is of interest, it is necessary to start a temperature simulator pass, e.g. using the H selection (Mode=2). This means at least one numerical solution to the BHTE, that is to say a time-intensive calculation.

The second exemplary embodiment realizes a different approach for the H controller, which in this case is called a "fast H controller". This is distinguished from the simple H controller by speed, since it does not require a numerical solution to the BHTE, but rather scales the provided (previously calculated in the T selection step) relative temperature increment distribution. In other words, fast H controller ascertains the power-absorption-based scaling factor K for a single H field strength value, and the respective temperature distribution is then formed on the basis of the scaling approach described further up.

The fast H controller therefore performs no time-consuming and memory space intensive advance calculation of multiple (for example 10) distributions, and is therefore particularly suitable for large data records, for example. Any desired H field strength value can be set and can be calculated in a resource saving manner. However, the fast H controller requires a prior pass in Mode=1. The two temperature distributions calculated there need to be available to the fast H controller as an input. Appropriate main memory space needs to be available.

The first exemplary embodiment of a simulator for a simulation tool therefore tends to require longer for execution, and also requires more hard disk memory (this is usually not a problem for systems that are customary today), but requires less main memory. Hence, this simulator is sometimes particularly suitable for execution on a PC, for example a standalone PC, or else a mobile computer such as a notebook or the like. By contrast, the second exemplary embodiment tends to work more quickly, particularly for processing H field strength values that are input by the user, and requires less hard disk memory space, but a larger main memory. Hence, the second exemplary embodiment of a simulator for a simulation tool tends to be suitable for use on powerful computers such as workstations or in mainframe systems.

Further modifications of the exemplary embodiments are conceivable which result in hybrid forms between the functionalities described for the first and second exemplary embodiments. It is thus conceivable for an executable file such as sim_t.exe from the first exemplary embodiment to write the basal temperature distribution and the relative temperature increment distribution to the hard disk, from where it can then be read in again by another executable file, such as sim_hr.exe, as described in the first exemplary embodiment. In this way, it is possible to provide a "fast H controller" without numerically solving the BHTE again, but the writing and reading of the data to and from the hard disk might slow down the cycle. Nevertheless, this modification may be advantageous for particular software configurations, hardware configurations and/or applications overall.

The invention is not limited to the exemplary embodiments described here and the aspects highlighted therein; on the contrary, a large number of modifications that are within the scope of action of a person skilled in the art are possible within the area indicated by the appended claims.

For the sake of completeness, the subject matter of the patent application establishing priority is repeated in briefly summarized form below:

1. A computer-aided simulation method for providing assistance in thermotherapy planning, wherein the thermotherapy comprises hyperthermia treatment of a tumor volume in a body volume of a human body, wherein the hyperthermia treatment comprises the application of a magnetic field in a treatment volume by means of a magnetic field applicator, wherein thermal energy can be introduced into at least one deposit volume by power absorption in the applied magnetic field by means of magnetic, paramagnetic and/or superparamagnetic nanoparticles deposited in the body, and wherein the method comprises the following steps:

in a first calculation step ("T selection"), calculation of a field strength value that needs to be set on the applicator on the basis of a geometric distribution of the nanoparticles and at least one prescribed temperature limit value which is not meant to be exceeded by the hyperthermia treatment;

in an optional second calculation step ("H controller"), calculation, for each field strength value from a plurality of prescribed field strength values, of a temperature distribution that is to be expected for at least part of the body volume; and provision of the calculated field strength value and optionally the calculated temperature distribution in order to provide assistance for the user in planning the thermotherapy.

2. The method according to subject 1, wherein the temperature limit value or one of a plurality of temperature limit values relates to a maximum temperature only within the treatment volume that is to be heated.

3. The method according to subject 2, wherein the temperature limit value relates to a prescribed temperature maximum in a range from 60° C. to 100° C., preferably 70° C. to 90° C., particularly 80° C., in the treatment volume.

4. The method according to one of the preceding subjects, wherein the temperature limit value or one of a plurality of temperature limit values relates to a maximum temperature outside the treatment volume that is to be heated.

5. The method according to subject 4, wherein the temperature limit value relates to a prescribed temperature maximum in a range from 40° C. to 45° C., particularly 43° C., outside the treatment volume.

6. The method according to one of the preceding subjects, wherein two temperature limit values which each relate to different volumes are used in the first calculation step ("T selection").

7. The method according to one of the preceding subjects, wherein the calculation result from the first calculation step ("T selection") is taken as a basis for automatically performing a third calculation step ("H selection") when the field strength value calculated in the first calculation step ("T selection") is greater than a prescribed maximum field strength value, particularly a maximum settable field strength value on the applicator, wherein a temperature distribution that is to be expected is calculated in the third calculation step ("H selection") for the prescribed maximum field strength value.

8. The method according to one of the preceding subjects, wherein no temperature limit value is used in the calculations in the second calculation step ("H controller") and/or in the third calculation step ("H selection").

9. The method according to one of the preceding subjects, wherein the calculations in the second calculation step ("H controller") are performed for a plurality of prescribed field strength values that can be set on the applicator, preferably between 3 and 20 field strength values, particularly preferably between 5 and 10 field strength values.

10. The method according to one of the preceding subjects, wherein the second calculation step ("H controller") is initiated after the first ("T selection") and possibly third ("H selection") calculation steps by a user input.

11. The method according to one of the preceding subjects, wherein output of the calculation results is followed by the performance of a fourth calculation step ("H selection"), in which a user input of field strength is accepted and, on the basis of the accepted field strength, a temperature distribution that is to be expected is calculated.

12. The method according to one of the preceding subjects, wherein the calculation of the field strength value that is to be set in the first calculation step ("T selection") does not comprise an iteration in which temperature distributions are calculated from chosen field strength values so as to iteratively arrive at the sought field strength value.

13. The method according to one of the preceding subjects, wherein the first calculation step ("T selection") has the following steps:
    calculation of an average power absorption density ("SAR_aver") in the applicator magnetic field in the deposit volume, wherein a relative power absorption density is calculated on the basis of a measured geometric distribution of the nanoparticles, a prescribed bioheat transfer equation is solved precisely once in order to obtain a basal temperature distribution without power absorption, and the bioheat transfer equation is solved precisely once in order to obtain a relative temperature increment distribution on the basis of the relative power absorption density; and wherein the relative power absorption density is scaled by a scaling factor which is obtained on the basis of the at least one prescribed temperature limit value, the basal temperature distribution and the relative temperature increment distribution;
    calculation, on the basis of the calculated average power absorption density and the calculated mass of the nanoparticles, of a reference power absorption rate ("SAR_Fe") which indicates the specific power absorption rate of an undiluted magnetic fluid containing the nanoparticles, for example; and
    calculation of a field strength value on the basis of the calculated reference power absorption rate and a prescribed characteristic curve which relates to a relationship between reference power absorption rate and applied field strength.

14. The method according to one of the preceding subjects, wherein the calculation of the temperature distributions in the second calculation step ("H controller") comprises precisely two calculations of temperature distributions regardless of the number of prescribed field strength values.

15. The method according to one of the preceding subjects, wherein the second calculation step ("H controller") has the following steps:
    calculation of a relative power absorption density distribution ("$\Delta SAR(x,y,z)$") and a relative average power absorption density ("$\Delta SAR\_aver$") on the basis of a measured geometric distribution of the nanoparticles;
    provision of a basal temperature distribution ("$T0(x,y,z)$") on the basis of a solution to a prescribed bioheat transfer equation without power absorption, and provision of a relative temperature increment distribution ("$\Delta T(x,y,z)$") on the basis of a solution to the bioheat transfer equation with the calculated relative power absorption density distribution ("$\Delta SAR(x,y,z)$");
    performance of the following steps for each field strength value from the plurality of prescribed field strength values:
        calculation of a reference power absorption rate ("$SAR\_Fe(i)$") which indicates the specific power absorption rate of an undiluted magnetic fluid containing the nanoparticles, for example, wherein the calculation is based on the respective field strength value and a prescribed characteristic curve which relates to a relationship between reference power absorption rate and applied field strength;
        calculation, on the basis of the reference power absorption rate ("$SAR\_Fe(i)$") and the calculated mass of the nanoparticles in the deposit volume, of an average power absorption density ("$SAR\_aver(i)$");
        calculation of a scaling factor ("$K(i)$") on the basis of the respective average power absorption density ("$SAR\_aver(i)$") and the relative average power absorption density ("$\Delta SAR\_aver$");
        calculation of a respective temperature distribution ("$T(x,y,z,i)$") on the basis of the basal temperature distribution ("$T0(x,y,z)$"), the relative temperature increment distribution ("$\Delta T(x,y,z)$") and the scaling factor ("$K(i)$").

16. A computer-aided simulation method ("T selection") for providing assistance in thermotherapy planning, wherein the thermotherapy comprises hyperthermia treatment of a tumor volume in a body volume of a human body, wherein the hyperthermia treatment comprises the application of a magnetic field in a treatment volume by means of a magnetic field applicator, wherein thermal energy can be introduced into at least one deposit volume by power absorption in the applied magnetic field by means of magnetic, paramagnetic and/or superparamagnetic nanoparticles deposited in the body, wherein the method relates to the calculation of a field strength that needs to be set on the applicator on the basis of a geometric distribution of the nanoparticles and at least one prescribed temperature limit value which is not meant to be exceeded by the hyperthermia treatment ("T selection"); wherein the method has the following steps:
    calculation of an average power absorption density ("SAR_aver") in the applicator magnetic field in the deposit volume, wherein a relative power absorption density is calculated on the basis of a measured geometric distribution of the nanoparticles, a prescribed bioheat transfer equation is solved precisely once in order to obtain a basal temperature distribution without power absorption, and the bioheat transfer equation is solved precisely once in order to obtain a relative temperature increment distribution on the basis of the relative power absorption density; and wherein the relative power absorption density is scaled by a scaling factor which is obtained on the basis of the at least one prescribed temperature limit value, the basal temperature distribution and the relative temperature increment distribution;

calculation, on the basis of the calculated average power absorption density and the calculated mass of the nanoparticles, of a reference power absorption rate ("SAR_Fe") which indicates the specific power absorption rate of an undiluted magnetic fluid containing the nanoparticles, for example;

calculation of a field strength value on the basis of the calculated reference power absorption rate and a prescribed characteristic curve which relates to a relationship between reference power absorption rate and applied field strength; and provision of the calculated field strength value for providing assistance for the user in planning the thermotherapy.

17. A computer-aided simulation method ("H controller") for providing assistance in thermotherapy planning, wherein the thermotherapy comprises hyperthermia treatment of a tumor volume in a body volume of a human body, wherein the hyperthermia treatment comprises the application of a magnetic field in a treatment volume by means of a magnetic field applicator, wherein thermal energy can be introduced into at least one deposit volume by power absorption in the applied magnetic field by means of magnetic, paramagnetic and/or superparamagnetic nanoparticles deposited in the body, wherein the method relates to the calculation, for each field strength value from a plurality of prescribed field strength values, of a temperature distribution that is to be expected for at least some of the body volume ("H controller"); and wherein the method has the following steps:

calculation of a relative power absorption density distribution ("$\Delta SAR(x,y,z)$") and a relative average power absorption density ("$\Delta SAR\_aver$") on the basis of a measured geometric distribution of the nanoparticles;

provision of a basal temperature distribution ("$T0(x,y,z)$") on the basis of a solution to a prescribed bioheat transfer equation without power absorption, and provision of a relative temperature increment distribution ("$\Delta T(x,y,z)$") on the basis of a solution to the bioheat transfer equation with the calculated relative power absorption density ("$\Delta SAR(x,y,z)$");

performance of the following steps for each field strength value from the plurality of prescribed field strength values:

calculation of a reference power absorption rate ("SAR_Fe(i)") which indicates the specific power absorption rate of an undiluted magnetic fluid containing the nanoparticles, for example, wherein the calculation is based on the respective field strength value and a prescribed characteristic curve which relates to a relationship between reference power absorption rate and applied field strength;

calculation, on the basis of the reference power absorption rate ("SAR_Fe(i)") and the calculated mass of the nanoparticles in the deposit volume, of an average power absorption density ("SAR_aver(i)");

calculation of a scaling factor ("K(i)") on the basis of the respective average power absorption density ("SAR_aver(i)") and the relative power absorption density ("$\Delta SAR\_aver$");

calculation of a respective temperature distribution ("T(x,y,z,i)") on the basis of the basal temperature distribution ("$T0(x,y,z)$"), the relative temperature increment distribution ("$\Delta T(x,y,z)$") and the scaling factor ("K(i)");

provision of the calculated temperature distributions in order to provide assistance for the user in planning the thermotherapy.

18. A computer program for carrying out the method according to one of the preceding subjects when the computer program is executed on a programmable computer device.

19. A data storage medium on which the computer program according to subject 18 is recorded.

20. A computer device designed for providing assistance in thermotherapy planning, wherein the thermotherapy comprises hyperthermia treatment of a tumor volume in a body volume of a human body, wherein the hyperthermia treatment comprises the application of a magnetic field in the treatment volume by means of a magnetic field applicator, wherein thermal energy can be introduced into at least one deposit volume by power absorption in the applied magnetic field by means of magnetic, paramagnetic and/or superparamagnetic nanoparticles deposited in the body, and wherein the computer device comprises the following components:

a first calculation component ("sim_t.exe") designed to calculate a field strength value that needs to be set on the applicator on the basis of a geometric distribution of the nanoparticles and at least one prescribed temperature limit value which is not meant to be exceeded by the hyperthermia treatment;

a second calculation component ("sim_hr.exe"), designed to optionally calculate, for each field strength value from a plurality of prescribed field strength values, a temperature distribution that is to be expected for at least some of the body volume; and a component for providing the calculated field strength value and optionally the calculated temperature distributions in order to provide assistance for the user in planning the thermotherapy.

21. A computer device designed for providing assistance in thermotherapy planning, wherein the thermotherapy comprises hyperthermia treatment of a tumor volume in a body volume of a human body, wherein the hyperthermia treatment comprises the application of a magnetic field in the treatment volume by means of a magnetic field applicator, wherein thermal energy can be introduced into at least one deposit volume by power absorption in the applied magnetic field by means of magnetic, paramagnetic and/or superparamagnetic nanoparticles deposited in the body, wherein the computer device has a component ("sim_t.exe") which is designed to calculate a field strength that needs to be set on the applicator on the basis of a geometric distribution of the nanoparticles and at least one prescribed temperature limit value which is not meant to be exceeded by the hyperthermia treatment; and wherein the component ("sim_t.exe") has the following modules:

a module for calculating an average power absorption density in the applicator magnetic field in the deposit volume, wherein a relative power absorption density is calculated on the basis of a measured geometric distribution of the nanoparticles, a prescribed bioheat transfer equation is solved precisely once in order to obtain a basal temperature distribution without power absorption, and the bioheat transfer equation is solved precisely once in order to obtain a relative temperature increment distribution on the basis of the relative power absorption density; and wherein the relative power absorption density is scaled by a scaling factor which is obtained on the basis of the at least one prescribed temperature limit value, the basal temperature distribution and the relative temperature increment distribution;

a module for calculating, on the basis of the calculated average power absorption density and the calculated mass of the nanoparticles, a reference power absorption rate which indicates the specific power absorption rate of an undiluted magnetic fluid containing the nanoparticles, for example;

a module for calculating a field strength value on the basis of the calculated reference power absorption rate and a prescribed characteristic curve which relates to a relationship between reference power absorption rate and applied field strength; and a module for providing the calculated field strength value in order to provide assistance for the user in planning the thermotherapy.

22. A computer device designed for providing assistance in thermotherapy planning, wherein the thermotherapy comprises hyperthermia treatment of a tumor volume in a body volume of a human body, wherein the hyperthermia treatment comprises the application of a magnetic field in the treatment volume by means of a magnetic field applicator, wherein thermal energy can be introduced into at least one deposit volume by power absorption in the applied magnetic field by means of magnetic, paramagnetic and/or superparamagnetic nanoparticles deposited in the body, wherein the computer device has a component ("sim_hr.exe") which is designed to calculate, for each field strength value from a plurality of prescribed field strength values, a temperature distribution that is to be expected for at least some of the body volume; and wherein the component ("sim_hr.exe") has the following modules:

a module for calculating a relative power absorption density distribution and a relative average power absorption density on the basis of a measured geometric distribution of the nanoparticles;

a module for providing a basal temperature distribution on the basis of a solution to a prescribed bioheat transfer equation without power absorption, and providing a relative temperature increment distribution on the basis of a solution to the bioheat transfer equation with the calculated relative power absorption density distribution;

a module for performing the following steps for each field strength value from the plurality of prescribed field strength values:

calculation of a reference power absorption rate which indicates the specific power absorption rate of an undiluted magnetic fluid containing the nanoparticles, for example, wherein the calculation is based on the respective field strength value and a prescribed characteristic curve which relates to a relationship between reference power absorption rate and applied field strength;

calculation, on the basis of the reference power absorption rate and the calculated mass of the nanoparticles in the deposit volume, of an average power absorption density;

calculation of a scaling factor on the basis of the respective average power absorption density and the relative power absorption density;

calculation of a respective temperature distribution on the basis of the basal temperature distribution, the relative temperature increment distribution and the scaling factor;

a module for providing the calculated temperature distributions in order to provide assistance for the user in planning the thermotherapy.

23. A system, comprising a computer device according to one of subjects 20 to 22 and a magnetic field applicator.

24. A system, comprising a computer program according to subject 18, a data storage medium according to subject 19, a computer device according to one of subjects 20 to 22 or a system according to subject 23, and also comprising a magnetic fluid containing magnetic nanoparticles.

25. A method for controlled heating of an organ or tissue, containing the steps of A) introduction of magnetic, paramagnetic and/or superparamagnetic particles into an organ volume or tissue volume, B) ascertainment of the particle quantity and/or distribution in the organ volume or tissue volume, C) calculation of a field strength that is able to be set on the basis of the method according to subject 1 or 16 or of a temperature distribution on the basis of the method according to subject 17, D) deposition of thermal energy by means of application of a magnetic field, wherein the applied field strength corresponds to the calculated field strength or to the field strength derived from a calculated temperature distribution, in each case with a deviation of +/−10%, preferably +/−5%, particularly +/−1%.

26. A method for treating a tumor in a patient, containing the steps of

A) introduction of magnetic, paramagnetic and/or superparamagnetic particles into a tumor volume, B) ascertainment of the particle quantity and/or distribution in the tumor volume, C) calculation of a field strength that is able to be set on the basis of the method according to subject 1 or 16 or of a temperature distribution on the basis of the method according to subject 17, D) deposition of thermal energy by means of application of a magnetic field, wherein the applied field strength corresponds to the calculated field strength or to the field strength derived from a calculated temperature distribution, in each case with a deviation of +/−10%, preferably +/−5%, particularly +/−1%.

The invention claimed is:

1. A computer-aided simulation method for providing assistance in thermotherapy planning, wherein the thermotherapy comprises hyperthermia treatment of a tumor volume in a body volume of a human body, wherein the hyperthermia treatment comprises the application of a magnetic field in a treatment volume by means of a magnetic field applicator, wherein thermal energy can be introduced into at least one deposit volume by power absorption in the applied magnetic field by means of magnetic, paramagnetic and/or superparamagnetic nanoparticles deposited in the body, and wherein the method comprises the following steps:

in a first calculation step ("T selection"), calculation of a field strength value that needs to be set on the applicator on the basis of a geometric distribution of the nanoparticles and at least one prescribed temperature limit value which is not meant to be exceeded by the hyperthermia treatment, wherein the field strength value is calculated in the first calculation step ("T selection") on the basis of a prescribed characteristic curve which indicates a relationship between (reference) power absorption rate and field strength;

in an optional second calculation step ("H controller", "fast H controller"), calculation of the temperature distribution that is to be expected for at least part of the body volume for each field strength value from a plurality of prescribed field strength values, and/or
a user-defined field strength value; and
provision of the calculated field strength value and optionally of at least one calculated temperature distribution for the purpose of supporting the user in planning the thermotherapy.

2. The method as claimed in claim 1, wherein the temperature limit value or one of a plurality of temperature limit values relates to a maximum temperature only within the treatment volume that is to be heated, wherein preferably the temperature limit value relates to a prescribed temperature maximum in a range from 60° C. to 100° C., preferably 70° C. to 90° C., particularly 80° C., in the treatment volume.

3. The method as claimed in claim 1, wherein the temperature limit value or one of a plurality of temperature limit values relates to a maximum temperature outside the treatment volume that is to be heated, wherein preferably the temperature limit value relates to a prescribed temperature maximum in a range from 40° C. to 45° C., particularly 43° C., outside the treatment volume.

4. The method as claimed in claim 1, wherein two temperature limit values which each relate to different volumes are used in the first calculation step ("T selection").

5. The method as claimed in claim 1, wherein the calculation result from the first calculation step ("T selection") is taken as a basis for automatically performing a third calculation step ("H selection") when the field strength value calculated in the first calculation step ("T selection") is greater than a prescribed maximum field strength value, particularly a maximum settable field strength value on the applicator, wherein a temperature distribution that is to be expected is calculated in the third calculation step ("H selection") for the prescribed maximum field strength value.

6. The method as claimed in claim 1, wherein no temperature limit value is used in the calculations in the second calculation step ("H controller", "fast H controller") and/or in the third calculation step ("H selection").

7. The method as claimed in claim 1, wherein the calculations in the second calculation step ("H controller") are performed for a plurality of prescribed field strength values that can be set on the applicator, preferably between 3 kA/m and 20 kA/m, particularly preferably between 5 kA/m and 10 kA/m.

8. The method as claimed in claim 1, wherein the calculation of the field strength value that is to be set in the first calculation step ("T selection") does not comprise an iteration in which temperature distributions are calculated from chosen field strength values so as to iteratively arrive at the sought field strength value.

9. The method as claimed in claim 1, wherein the first calculation step ("T selection") has the following steps:
calculation of an average power absorption density ("SAR_aver") in the applicator magnetic field in the deposit volume, wherein a relative power absorption density ("$\Delta$SAR(x,y,z)") is calculated on the basis of a measured geometric distribution of the nanoparticles, a bioheat transfer equation describing the model is numerically solved precisely once in order to obtain a basal temperature distribution ("T0(x,y,z)") without power absorption, and the bioheat transfer equation is numerically solved precisely once in order to obtain a relative temperature increment distribution ("$\Delta$T(x,y,z)") on the basis of the relative power absorption density; and wherein the relative power absorption density ("$\Delta$SAR(x,y,z)") is scaled by a temperature-based scaling factor ("K") which is obtained on the basis of the at least one prescribed temperature limit value, the basal temperature distribution and the relative temperature increment distribution;
calculation, on the basis of the calculated average power absorption density and the calculated mass of the nanoparticles, of a reference power absorption rate ("SAR_Fe") which indicates the specific power absorption rate of an undiluted magnetic fluid containing the nanoparticles, for example;
calculation of a field strength value ("H") on the basis of the calculated reference power absorption rate ("SAR_Fe") and a prescribed characteristic curve which relates to a relationship between reference power absorption rate and applied field strength ("H"); and
optional calculation of a respective temperature distribution ("T(x,y,z)") on the basis of the basal temperature distribution ("T0(x,y,z)"), the relative temperature increment distribution ("$\Delta$T(x,y,z)") and the temperature-based scaling factor ("K").

10. The method as claimed in claim 1, wherein in the second calculation step ("fast H controller"), regardless of the number of prescribed and/or user-defined field strength values, a provided (previously calculated in the first calculation step) basal temperature distribution ("T0(x,y,z)") and/or a provided (previously calculated in the first calculation step) relative temperature increment distribution ("$\Delta$T(x,y,z)") are used.

11. The method as claimed in claim 1, wherein in the second calculation step ("H controller"), regardless of the number of prescribed and/or user-defined field strength values, no more than two temperature distributions are calculated, namely a basal temperature distribution ("T0(x,y,z)") and/or a relative temperature increment distribution ("$\Delta$T(x,y,z)").

12. The method as claimed in claim 1, wherein in the second calculation step (H controller", "fast H controller"), the temperature distribution that is to be expected is calculated by means of power-absorption-based scaling ("K") of a calculated or provided relative temperature increment distribution ("$\Delta$T(x,y,z)").

13. The method as claimed in claim 12, wherein the second calculation step ("H controller", "fast H controller") has the following steps:
calculation of a relative power absorption density distribution ("$\Delta$SAR(x,y,z)") and a relative average power absorption density ("$\Delta$SAR_aver") on the basis of a measured geometric distribution of the nanoparticles;
provision of a basal temperature distribution ("T0(x,y,z)") on the basis of a numerical solution to a bioheat transfer equation describing the model without power absorption, and provision of a relative temperature increment distribution ("$\Delta$T(x,y,z)") on the basis of a numerical solution to the bioheat transfer equation with the calculated relative power absorption density distribution ("$\Delta$SAR(x,y,z)");
performance of the following steps for each field strength value from the plurality of prescribed field strength values and/or the user-defined field strength value:
calculation of a reference power absorption rate ("SAR_Fe") which indicates the specific power absorption rate of an undiluted magnetic fluid containing the nanoparticles, for example, wherein the calculation is based on the respective field strength value ("H") and a prescribed characteristic curve which relates to a relationship between reference power absorption rate ("SAR_Fe") and applied field strength ("H");

calculation, on the basis of the reference power absorption rate ("SAR_Fe") and the calculated mass of the nanoparticles in the deposit volume, of an average power absorption density ("SAR_aver");

calculation of a power-absorption-based scaling factor ("K") on the basis of the respective average power absorption density ("SAR_aver") and the relative average power absorption density ("ΔSAR_aver");

calculation of a respective temperature distribution ("T(x,y,z)") on the basis of the basal temperature distribution ("T0(x,y,z)"), the relative temperature increment distribution ("ΔT(x,y,z)") and the power-absorption-based scaling factor ("K").

14. A computer-aided simulation method ("T selection") for providing assistance in thermotherapy planning, wherein the thermotherapy comprises hyperthermia treatment of a tumor volume in a body volume of a human body, wherein the hyperthermia treatment comprises the application of a magnetic field in a treatment volume by means of a magnetic field applicator, wherein thermal energy can be introduced into at least one deposit volume by power absorption in the applied magnetic field by means of magnetic, paramagnetic and/or superparamagnetic nanoparticles deposited in the body, wherein the method relates to the calculation of a field strength that needs to be set on the applicator on the basis of a geometric distribution of the nanoparticles and at least one prescribed temperature limit value which is not meant to be exceeded by the hyperthermia treatment ("T selection");

and wherein the field strength value is calculated on the basis of a prescribed characteristic curve which indicates a relationship between (reference) power absorption rate and field strength.

15. The method as claimed in claim 14, wherein the method has the following steps ("T selection"):

calculation of an average power absorption density ("SAR_aver") in the applicator magnetic field in the deposit volume, wherein a relative power absorption density ("ΔSAR(x,y,z)") is calculated on the basis of a measured geometric distribution of the nanoparticles, a bioheat transfer equation describing the model is numerically solved precisely once in order to obtain a basal temperature distribution ("T0(x,y,z)") without power absorption, and the bioheat transfer equation is numerically solved precisely once in order to obtain a relative temperature increment distribution ("ΔT(x,y,z)") on the basis of the relative power absorption density; and wherein the relative power absorption density ("ΔSAR(x,y,z)") is scaled by a temperature-based scaling factor ("K") which is obtained on the basis of the at least one prescribed temperature limit value, the basal temperature distribution and the relative temperature increment distribution;

calculation, on the basis of the calculated average power absorption density and the calculated mass of the nanoparticles, of a reference power absorption rate ("SAR_Fe") which indicates the specific power absorption rate of an undiluted magnetic fluid containing the nanoparticles, for example;

calculation of a field strength value ("H") on the basis of the calculated reference power absorption rate ("SAR_Fe") and a prescribed characteristic curve which relates to a relationship between reference power absorption rate ("SAR_Fe") and applied field strength ("H");

optional calculation of a respective temperature distribution ("T(x,y,z)") on the basis of the basal temperature distribution ("T0(x,y,z)"), the relative temperature increment distribution ("ΔT(x,y,z)") and the temperature-based scaling factor ("K");

provision of the calculated field strength value ("H") in order to provide assistance for the user in planning the thermotherapy; and optional provision of the calculated temperature distribution ("T(x,y,z)") in order to provide assistance for the user in planning the thermotherapy.

16. A computer-aided simulation method ("H controller", "fast H controller") for providing assistance in thermotherapy planning, wherein the thermotherapy comprises hyperthermia treatment of a tumor volume in a body volume of a human body, wherein the hyperthermia treatment comprises the application of a magnetic field in a treatment volume by means of a magnetic field applicator, wherein thermal energy can be introduced into at least one deposit volume by power absorption in the applied magnetic field by means of magnetic, paramagnetic and/or superparamagnetic nanoparticles deposited in the body, wherein the method relates to the calculation, for each field strength value from a plurality of prescribed field strength values and/or a user-defined field strength value, of a temperature distribution that is to be expected for at least some of the body volume;

and wherein the temperature distribution that is to be expected is calculated by means of power-absorption-based scaling ("K") of a calculated or provided relative temperature increment distribution ("ΔT(x,y,z)").

17. The method as claimed in claim 16, wherein, regardless of the number of prescribed and/or user-defined field strength values, a provided (previously calculated in the T selection step) basal temperature distribution ("T0(x,y,z)") and/or a provided (previously calculated in the T selection step) relative temperature increment distribution ("ΔT(x,y,z)") is/are used ("fast H controller"), preferably, wherein no more than two temperature distributions are calculated ("H controller"), namely a basal temperature distribution ("T0(x,y,z)") and/or a relative temperature increment distribution ("ΔT(x,y,z)").

18. The method as claimed in claim 16, wherein the method has the following steps ("H controller", "fast H controller"):

calculation of a relative power absorption density distribution ("ΔSAR(x,y,z)") and a relative average power absorption density ("ΔSAR_aver") on the basis of a measured geometric distribution of the nanoparticles;

provision of a basal temperature distribution ("T0(x,y,z)") on the basis of a numerical solution to a bioheat transfer equation describing the model without power absorption, and provision of a relative temperature increment distribution ("ΔT(x,y,z)") on the basis of a numerical solution to the bioheat transfer equation with the calculated relative power absorption density ("ΔSAR(x,y,z)");

performance of the following steps for each field strength value from the plurality of prescribed field strength values and/or the user-defined field strength value:

calculation of a reference power absorption rate ("SAR_Fe") which indicates the specific power absorption rate of an undiluted magnetic fluid containing the nanoparticles, for example, wherein the calculation is based on the respective field strength value ("H") and a prescribed characteristic curve which relates to a relationship between reference power absorption rate ("SAR_Fe") and applied field strength ("H");

calculation, on the basis of the reference power absorption rate ("SAR_Fe") and the calculated mass of the nanoparticles in the deposit volume, of an average power absorption density ("SAR_aver");

calculation of a power-absorption-based scaling factor ("K") on the basis of the respective average power absorption density ("SAR_aver") and the relative power absorption density ("ΔSAR_aver");

calculation of a respective temperature distribution ("T(x,y,z)") on the basis of the basal temperature distribution ("T0(x,y,z)"), the relative temperature increment distribution ("ΔT(x,y,z)") and the power-absorption-based scaling factor ("K");

provision of the calculated temperature distributions in order to provide assistance for the user in planning the thermotherapy.

19. A computer program for carrying out the method as claimed in claim 1, 10, or 12, when the computer program is executed on a programmable computer device.

20. A computer device designed for providing assistance in thermotherapy planning ("T selection"), wherein the thermotherapy comprises hyperthermia treatment of a tumor volume in a body volume of a human body, wherein the hyperthermia treatment comprises the application of a magnetic field in the treatment volume by means of a magnetic field applicator, wherein thermal energy can be introduced into at least one deposit volume by power absorption in the applied magnetic field by means of magnetic, paramagnetic and/or superparamagnetic nanoparticles deposited in the body, wherein the computer device has a component ("sim_t.exe", "mainsubroutine_sim_t_voxel_win") which is designed to calculate a field strength that needs to be set on the applicator on the basis of a geometric distribution of the nanoparticles and at least one prescribed temperature limit value which is not meant to be exceeded by the hyperthermia treatment;

and wherein the component ("sim_t.exe", "mainsubroutine_sim_t_voxel_win") has a module for calculating the field strength value on the basis of a prescribed characteristic curve, wherein the characteristic curve indicates a relationship between power absorption rate and field strength.

21. The computer device as claimed in claim 20, wherein the computer device has the following module ("T selection"):

a module for calculating an average power absorption density in the applicator magnetic field in the deposit volume, wherein a relative power absorption density is calculated on the basis of a measured geometric distribution of the nanoparticles, a bioheat transfer equation describing the model is numerically solved precisely once in order to obtain a basal temperature distribution without power absorption, and the bioheat transfer equation is numerically solved precisely once in order to obtain a relative temperature increment distribution on the basis of the relative power absorption density; and wherein the relative power absorption density is scaled by a scaling factor which is obtained on the basis of the at least one prescribed temperature limit value, the basal temperature distribution and the relative temperature increment distribution ("temperature-based scaling factor");

a module for calculating, on the basis of the calculated average power absorption density and the calculated mass of the nanoparticles, a reference power absorption rate which indicates the specific power absorption rate of an undiluted magnetic fluid containing the nanoparticles, for example;

a module for calculating a field strength value on the basis of the calculated reference power absorption rate and a prescribed characteristic curve which relates to a relationship between reference power absorption rate and applied field strength;

a module for providing the calculated field strength value in order to provide assistance for the user in planning the thermotherapy, optionally a module for calculating respective temperature distribution on the basis of the basal temperature distribution, the relative temperature increment distribution and the temperature-based scaling factor; and optionally a module for providing the calculated temperature distributions in order to provide assistance for the user in planning the thermotherapy.

22. A computer device designed for providing assistance in thermotherapy planning ("H controller", "fast H controller"), wherein the thermotherapy comprises hyperthermia treatment of a tumor volume in a body volume of a human body, wherein the hyperthermia treatment comprises the application of a magnetic field in the treatment volume by means of a magnetic field applicator, wherein thermal energy can be introduced into at least one deposit volume by power absorption in the applied magnetic field by means of magnetic, paramagnetic and/or superparamagnetic nanoparticles deposited in the body, wherein the computer device has a component ("sim_hr.exe", "mainsubroutine_sim_hr_voxel_win") which is designed to calculate, for each field strength value from a plurality of prescribed field strength values and/or a user-defined field strength value, a temperature distribution that is to be expected for at least some of the body volume;

and wherein the component ("sim_hr.exe", "mainsubroutine_sim_hr_voxel_win") has a module for calculating the temperature distribution that is to be expected by means of power-absorption-based scaling ("K") of a calculated or provided temperature increment distribution ("ΔT(x,y,z)").

23. The computer device as claimed in claim 22, wherein the component ("mainsubroutine_sim_hr_voxel_win") is designed to calculate the temperature distribution that is to be expected in order to use, regardless of the number of prescribed and/or user-defined field strength values, a provided (previously calculated in mainsubroutine_sim_t_voxel_win) basal temperature distribution ("T0(x,y,z)") and/or a provided (previously calculated in mainsubroutine_sim_t_voxel_win) relative temperature increment distribution ("ΔT(x,y,z)") ("fast H controller").

24. The computer device as claimed in claim 23, wherein the component ("sim_hr.exe") for calculating the temperature distribution that is to be expected is designed to calculate, regardless of the number of prescribed and/or user-defined field strength values, no more than two temperature distributions ("H controller"), namely a basal temperature distribution ("T0(x,y,z)") and/or a relative temperature increment distribution ("ΔT(x,y,z)").

25. The computer device as claimed in claim 24, wherein the computer device has the following modules ("H controller", "fast H controller"):
- a module for calculating a relative power absorption density distribution and a relative average power absorption density on the basis of a measured geometric distribution of the nanoparticles;
- a module for providing a basal temperature distribution on the basis of a numerical solution to a bioheat transfer equation describing the model without power absorption, and providing a relative temperature increment distribution on the basis of a numerical solution to the bioheat transfer equation with the calculated relative power absorption density distribution;
- a module for performing the following steps for each field strength value from the plurality of prescribed field strength values and/or the user-defined field strength value:
    - calculation of a reference power absorption rate which indicates the specific power absorption rate of an undiluted magnetic fluid containing the nanoparticles, for example, wherein the calculation is based on the respective field strength value and a prescribed characteristic curve which relates to a relationship between reference power absorption rate and applied field strength;
    - calculation, on the basis of the reference power absorption rate and the calculated mass of the nanoparticles in the deposit volume, of an average power absorption density;
    - calculation of a power-absorption-based scaling factor on the basis of the respective average power absorption density and the relative power absorption density;
    - calculation of a respective temperature distribution on the basis of the basal temperature distribution, the relative temperature increment distribution and the power-absorption-based scaling factor;
- a module for providing the calculated temperature distributions in order to provide assistance for the user in planning the thermotherapy.

26. A system, comprising a computer device as claimed in one of claim 20, or 22 and a magnetic field applicator.

27. A system, comprising a computer program for carrying out the method as claimed in one of claim 1, 14 or 16, when the computer program is executed on a programmable computer device,
- a computer device designed for providing assistance in thermotherapy planning ("T selection"), wherein the thermotherapy comprises hyperthermia treatment of a tumor volume in a body volume of a human body, wherein the hyperthermia treatment comprises the application of a magnetic field in the treatment volume by means of a magnetic field applicator, wherein thermal energy can be introduced into at least one deposit volume by power absorption in the applied magnetic field by means of magnetic, paramagnetic and/or superparamagnetic nanoparticles deposited in the body, wherein the computer device has a component ("sim_t.exe", "mainsubroutine_sim_t_voxel_win") which is designed to calculate a field strength that needs to be set on the applicator on the basis of a geometric distribution of the nanoparticles and at least one prescribed temperature limit value which is not meant to be exceeded by the hyperthermia treatment; and wherein the component ("sim_t.exe", "mainsubroutine_sim_t_voxel_win") has a module for calculating the field strength value on the basis of a prescribed characteristic curve, wherein the characteristic curve indicates a relationship between power absorption rate and field strength, or
- a system comprising such a computer device and a magnetic field applicator, and also comprising a magnetic fluid containing magnetic nano-particles.

28. A system, comprising a computer program for carrying out the method as claimed in one of claim 1, 14 or 16, when the computer program is executed on a programmable computer device,
- a computer device designed for providing assistance in thermotherapy planning ("H controller", "fast H controller"), wherein the thermotherapy comprises hyperthermia treatment of a tumor volume in a body volume of a human body, wherein the hyperthermia treatment comprises the application of a magnetic field in the treatment volume by means of a magnetic field applicator, wherein thermal energy can be introduced into at least one deposit volume by power absorption in the applied magnetic field by means of magnetic, paramagnetic and/or superparamagnetic nanoparticles deposited in the body, wherein the computer device has a component ("sim_hr.exe", "mainsubroutine_sim_hr_voxel_win") which is designed to calculate, for each field strength value from a plurality of prescribed field strength values and/or a user-defined field strength value, a temperature distribution that is to be expected for at least some of the body volume; and wherein the component ("sim_hr.exe", "mainsubroutine_sim_hr_voxel_win") has a module for calculating the temperature distribution that is to be expected by means of power-absorption-based scaling ("K") of a calculated or provided temperature increment distribution ("$\Delta T(x,y,z)$"), or
- a system comprising such a computer device and a magnetic field applicator, and also comprising a magnetic fluid containing magnetic nano-particles.

* * * * *